US011763145B2

(12) United States Patent
Liu et al.

(10) Patent No.: US 11,763,145 B2
(45) Date of Patent: Sep. 19, 2023

(54) ARTICLE RECOMMENDATION METHOD AND APPARATUS, COMPUTER DEVICE, AND STORAGE MEDIUM

(71) Applicant: Tencent Technology (Shenzhen) Company Limited, Shenzhen (CN)

(72) Inventors: Yi Liu, Guangdong (CN); Lantao Hu, Guangdong (CN); Bo Zhang, Guangdong (CN); Feng Xia, Guangdong (CN); Leyu Lin, Guangdong (CN); Zhe Feng, Guangdong (CN); Lei Chen, Guangdong (CN); Jun Rao, Guangdong (CN); Shukai Liu, Guangdong (CN); Zhijie Qiu, Guangdong (CN); Zhenlong Sun, Guangdong (CN); Liangdong Wang, Guangdong (CN)

(73) Assignee: Tencent Technology (Shenzhen) Company Limited, Shenzhen (CN)

( * ) Notice: Subject to any disclaimer, the term of this patent is extended or adjusted under 35 U.S.C. 154(b) by 705 days.

(21) Appl. No.: 16/945,066

(22) Filed: Jul. 31, 2020

(65) Prior Publication Data
US 2020/0364506 A1 Nov. 19, 2020

Related U.S. Application Data

(63) Continuation of application No. PCT/CN2019/086374, filed on May 10, 2019.

(30) Foreign Application Priority Data

May 25, 2018 (CN) .......................... 201810515869.8

(51) Int. Cl.
G06N 3/08 (2023.01)
A61B 5/16 (2006.01)
(Continued)

(52) U.S. Cl.
CPC ............... *G06N 3/08* (2013.01); *A61B 5/165* (2013.01); *G06F 18/2155* (2023.01); *G06N 5/022* (2013.01); *G06V 40/20* (2022.01)

(58) Field of Classification Search
CPC .......... G06N 3/08; G06N 5/022; G06N 3/044; G06N 7/01; G06N 3/084; G06N 5/02;
(Continued)

(56) References Cited

U.S. PATENT DOCUMENTS 8,260,117 B1 * 9/2012 Xu ..................... H04N 21/4668
386/343
9,779,356 B2 * 10/2017 Driscoll ................ G06F 16/951
(Continued)

FOREIGN PATENT DOCUMENTS

CN 102654859 A 9/2012
CN 103488714 A 1/2014
(Continued)

OTHER PUBLICATIONS

Office action dated Sep. 2, 2020 for Chinese application 201810515869. 8, with search report, 6 pages.
(Continued)

*Primary Examiner* — Michael S Osinski
(74) *Attorney, Agent, or Firm* — Crowell & Moring LLP

(57) ABSTRACT

This application provides an article recommendation method and apparatus, a computer device, and a storage medium. The method includes: obtaining a historical reading article set of a to-be-analyzed target user, the historical reading article set comprising a plurality of historical articles that have been read by the target user at different reading moments; determining, for each historical article of the plurality of historical articles, first attention degree values between the each historical article and candidate reference historical articles having reading moments before that of the
(Continued)

each historical article, the first attention degree values reflecting a possibility that a user is recommended to read the historical article if the user has read the candidate reference historical articles; selecting at least one recommendation reference article from the candidate reference historical articles corresponding to the historical articles according to the first attention degree values between the historical articles and corresponding candidate reference historical articles; and determining, in a recommendable article set at least one candidate recommended article to be recommended to the target user based on the at least one recommendation reference article.

18 Claims, 11 Drawing Sheets

(51) Int. Cl.
 *G06N 5/022* (2023.01)
 *G06V 40/20* (2022.01)
 *G06F 18/214* (2023.01)

(58) Field of Classification Search
 CPC ... A61B 5/165; G06F 18/2155; G06F 16/337; G06F 16/9535; G06F 17/00; G06F 3/0482; G06F 16/24578; G06F 16/285; G06V 40/20; H04N 21/4668; H04N 21/4826; H04N 21/251; H04N 21/25891; H04N 21/4312; H04N 21/44222; H04N 21/44224; G06Q 30/0631; G06Q 30/02; G06Q 50/01; G06Q 30/0255
 See application file for complete search history.

(56) References Cited

U.S. PATENT DOCUMENTS

| | | | | |
|---|---|---|---|---|
| 9,864,951 | B1* | 1/2018 | Makhijani | G06Q 30/0282 |
| 10,148,375 | B2* | 12/2018 | Ling | H04N 21/26283 |
| 11,488,270 | B2* | 11/2022 | Srivastava | G06N 20/00 |
| 11,604,968 | B2* | 3/2023 | Ott | G06N 3/084 |
| 2015/0120712 | A1 | 4/2015 | Yi et al. | |
| 2015/0339692 | A1* | 11/2015 | Poreh | G06Q 30/06 705/7.35 |
| 2015/0339693 | A1* | 11/2015 | Poreh | G06Q 30/0206 705/7.35 |
| 2016/0255410 | A1* | 9/2016 | Itoh | H04N 21/4532 725/14 |
| 2016/0353235 | A1* | 12/2016 | Williams | H04W 4/02 |
| 2017/0090867 | A1* | 3/2017 | Lifar | G06F 7/24 |
| 2017/0091336 | A1* | 3/2017 | Royzner | G06F 16/435 |
| 2017/0091805 | A1* | 3/2017 | Tu | G06Q 30/0255 |
| 2017/0169040 | A1* | 6/2017 | Guan | G06F 16/738 |
| 2017/0171580 | A1 | 6/2017 | Hirsch et al. | |
| 2017/0188102 | A1* | 6/2017 | Zhang | H04N 21/4532 |
| 2017/0195731 | A1* | 7/2017 | Girlando | H04N 21/4312 |
| 2017/0337250 | A1* | 11/2017 | Li | G06Q 10/101 |
| 2018/0011937 | A1* | 1/2018 | Tikhonov | G06F 16/9536 |
| 2018/0039631 | A1* | 2/2018 | Gupta | H04L 67/01 |
| 2018/0060749 | A1* | 3/2018 | Yan | G06Q 50/01 |
| 2018/0081503 | A1* | 3/2018 | Green | G06N 3/08 |
| 2018/0083901 | A1* | 3/2018 | McGregor, Jr | H04L 51/02 |
| 2018/0107645 | A1 | 4/2018 | Payne et al. | |
| 2018/0330248 | A1* | 11/2018 | Burhanuddin | G06N 7/01 |
| 2019/0095800 | A1* | 3/2019 | Asbag | G06F 18/2415 |
| 2019/0163758 | A1* | 5/2019 | Zhivotvorev | G06F 16/24578 |
| 2019/0394529 | A1* | 12/2019 | Hou | H04N 21/4722 |
| 2020/0134696 | A1* | 4/2020 | Lardeux | G06Q 30/0254 |
| 2020/0380540 | A1* | 12/2020 | Fox | G06N 20/00 |
| 2023/0004608 | A1* | 1/2023 | Li | G06V 20/30 |

FOREIGN PATENT DOCUMENTS

| | | |
|---|---|---|
| CN | 103559262 A | 2/2014 |
| CN | 103678620 A | 3/2014 |
| CN | 104050163 A | 9/2014 |
| CN | 105474255 A | 4/2016 |
| CN | 105989045 A | 10/2016 |
| CN | 107766547 A | 3/2018 |

OTHER PUBLICATIONS

International Search Report and Written Opinion dated Aug. 12, 2019 for PCT Application No. PCT/CN2019/086374, nine pages.

* cited by examiner

ARTICLE RECOMMENDATION METHOD AND APPARATUS, COMPUTER DEVICE, AND STORAGE MEDIUM

RELATED APPLICATION

This application claims is a continuation of the PCT International Patent Application No. PCT/CN2019/086374, entitled "ARTICLE RECOMMENDATION METHOD AND APPARATUS, COMPUTER DEVICE, AND STORAGE MEDIUM" and filed with the China National Intellectual Property Administration on May 10, 2019, which claims priority to Chinese Patent Application No. 201810515869.8, entitled "ARTICLE RECOMMENDATION METHOD AND APPARATUS, COMPUTER DEVICE, AND STORAGE MEDIUM" filed with the China National Intellectual Property Administration on May 25, 2018, which are incorporated herein by reference in their entireties.

FIELD OF THE TECHNOLOGY

This application relates to the field of data processing technologies, and in particular, to an article recommendation method and apparatus, a computer device, and a storage medium.

BACKGROUND OF THE DISCLOSURE

With continuous development of communication networks, an increasing quantity of articles can be read by users through various article publishing platforms (for example, various official accounts in instant messaging platforms) on the Internet.

To attract users to read articles in an article publishing platform, the article publishing platform recommends articles to the users according to historical articles that have been read by the users. However, currently, when articles are recommended to users, articles with similar content are recommended to the users according to reading histories of the users. For example, a content-based recommendation technology may determine, according to historical articles that have been read by users, articles having content similar to that of articles that the users have read, and recommending the similar articles to the users.

However, most of the articles recommended for the users are similar to the articles that have been read by the users, and consequently, diversity of article recommendation is relatively poor.

SUMMARY

In view of this, this application provides an article recommendation method and apparatus, a computer device, and a storage medium, to improve diversity of article recommendation.

To achieve the foregoing objective, according to an aspect, this application provides an article recommendation method, including:
  obtaining, by a computer device, a historical reading article set of a to-be-analyzed target user, the historical reading article set comprising a plurality of historical articles that have been read by the target user at different reading moments;
  determining, by the computer device for each historical article of the plurality of historical articles, first attention degree values between the each historical article and candidate reference historical articles having reading moments before that of the each historical article, the first attention degree values reflecting a possibility that a user is recommended to read the historical article if the user has read the candidate reference historical articles;
  selecting, by the computer device, at least one recommendation reference article from the candidate reference historical articles corresponding to the historical articles according to the first attention degree values between the historical articles and corresponding candidate reference historical articles; and
  determining, by the computer device in a recommendable article set at least one candidate recommended article to be recommended to the target user based on the at least one recommendation reference article According to another aspect, this application further provides an article recommendation apparatus, comprising a memory for storing computer instructions and a processor configured to execute the computer instructions to:
  obtain a historical reading article set of a to-be-analyzed target user, the historical reading article set comprising a plurality of historical articles that have been read by the target user at different reading moments;
  determine, for each historical article of the plurality of historical articles, first attention degree values between the each historical article and candidate reference historical article having reading moments before that of the each historical article, the first attention degree values reflecting a possibility that a user is recommended to read the historical article if the user has read the candidate reference historical article;
  select at least one recommendation reference article from the candidate reference historical articles corresponding to the historical articles according to the first attention degree values between the historical articles and corresponding candidate reference historical article; and
  determine, in a recommendable article set, at least one candidate recommended article to be recommended to the target user based on the at least one recommendation reference article.

According to still another aspect, this application further provides a computer-readable non-transitory storage medium, the storage medium storing a computer program, the computer program when executed by a processor, is configured to cause the processor to:
  obtain a historical reading article set of a to-be-analyzed target user, the historical reading article set comprising a plurality of historical articles that have been read by the target user at different reading moments;
  determine, for each historical article of the plurality of historical articles, first attention degree values between the each historical article and candidate reference historical article having reading moments before that of the each historical article, the first attention degree values reflecting a possibility that a user is recommended to read the historical article if the user has read the candidate reference historical article;
  select at least one recommendation reference article from the candidate reference historical articles corresponding to the historical articles according to the first attention degree values between the historical articles and corresponding candidate reference historical article; and determine, in a recommendable article set, at least one candidate recommended article to be recommended to the target user based on the at least one recommendation reference article.

It can be learned from the above that, in the embodiments of this application, for a historical article that has been read by a user, attention degrees between other historical articles read by the user before the historical article is read and the historical article are analyzed. Because the attention degree between two articles may reflect a possibility that a user is recommended to read the other article if the user reads one article, a historical article representing a relatively low possibility of recommending an article to a target user may be determined in a historical reading article set according to the determined attention degrees between each article and other articles, and a category and content of the historical article do not belong to categories and content of articles that the user often reads. Therefore, a candidate recommended article is recommended to the user by using the historical article as a recommendation reference article, thereby improving diversity of the determined candidate recommended articles, and further improving diversity of articles recommended to the user.

BRIEF DESCRIPTION OF THE DRAWINGS

To describe the technical solutions in the embodiments of this application or the related art more clearly, the following briefly describes the accompanying drawings to facilitate the description of the embodiments or the related technology. The accompanying drawings are merely examples, and a person of ordinary skill in the art may still derive other drawings from the accompanying drawings without creative efforts.

DESCRIPTION OF EMBODIMENTS

An article recommendation method in the embodiments of this application is applicable to various article publishing platforms, to determine recommended articles for different users in the article publishing platforms, thereby improving diversity of articles recommended to the users. For example, a news media platform recommends news articles for different users, and a social platform or an official account accessing a social platform recommends articles to users.

Figure 1:
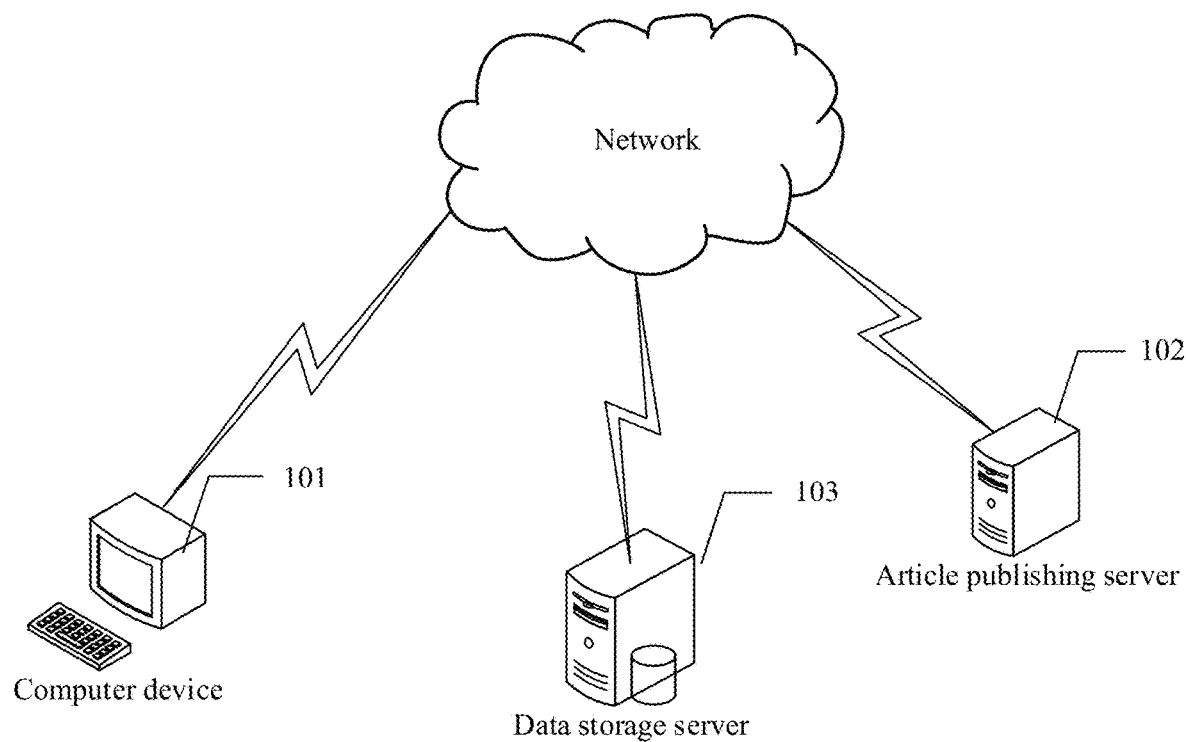
FIG. 1 shows a schematic diagram of a system to which an article recommendation method is applicable according to an embodiment of this application.

For ease of understanding, FIG. 1 shows a schematic diagram of components of an article recommendation system of this application.

It can be learned from FIG. 1 that, the article recommendation system may include: a computer device 101 and at least one article publishing server 102.

The article publishing server 102 is configured to publish a plurality of articles for users to read, and record articles read by different users at different moments (or different times, or different time durations). For ease of distinguishing, an article read by a user is referred to as a historical article.

The computer device 101 is configured to determine, based on a plurality of historical articles read by each user, a recommended article that is suitable for recommendation to the user.

The computer device 101 may further send information of the recommended article determined to be recommended to the user to the article publishing server.

Optionally, the article recommendation system may further include a data storage server 103. The data storage server may store user data, such as a user profile and a historical reading record of a user, generated by at least one article publishing server. The user profile may include user attribute information such as gender, age, education background, and location of a user. The historical reading record may include information such as articles that have been read by a user and sources related to the articles.

Correspondingly, the computer device 101 may obtain a historical reading record of a user from the data storage server 103, and determine, according to the historical reading record of the user, an article to be recommended to the user.

The historical articles that have been read by the user on which the computer device 101 monitors may be from one or more article publishing servers in an article publishing platform, or may be from article publishing servers of a plurality of article publishing platforms.

For an article publishing platform, the computer device 101 may be a server or a terminal that is individually disposed independently of the article publishing server. Alternatively, the computer device 101 may be the same server as the article publishing server. That is, the computer device has functions of publishing articles and determining articles recommended to a user.

Figure 2:
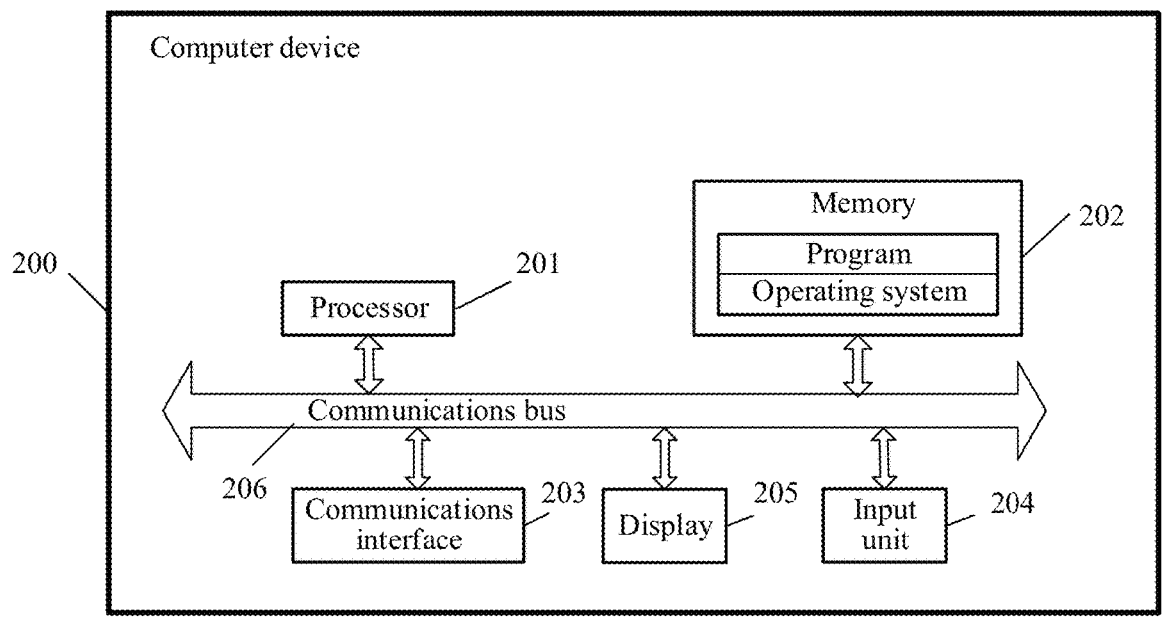
FIG. 2 shows a schematic diagram of a computer device to which an article recommendation method is applicable according to an embodiment of this application.

For ease of understanding the computer device, for example, FIG. 2 shows a schematic diagram of a composition of a computer device of this application.

As shown in FIG. 2, the computer device 200 may include a processor 201, a memory 202, a communications interface 203, an input unit 204, a display 205, and a communications bus 206.

The processor 201, the memory 202, the communications interface 203, the input unit 204, and the display 205 all communicate with each other by using the communications bus 206.

In this embodiment of this application, the processor 201 may be a central processing unit (CPU), an application-specific integrated circuit (ASIC), a digital signal processor (DSP), a field programmable gate array (FPGA), another programmable logic device, or the like.

The processor 201 may invoke a program stored in the memory 202, and may perform the following operations performed on a server side in FIG. 3 to FIG. 9.

The memory 202 is configured to store one or more programs. The program may include program code, the program code including a computer operation instruction. In this embodiment of this application, the memory stores at least a program for implementing the following functions:

obtaining, a historical reading article set of a to-be-analyzed target user, the historical reading article set comprising a plurality of historical articles that have been read by the target user at different reading moments;

determining, for each historical article of the plurality of historical articles, first attention degree values between the each historical article and candidate reference historical articles having reading moments before that of the each historical article, the first attention degree values reflecting a possibility that a user is recommended to read the historical article if the user has read the candidate reference historical articles;

selecting at least one recommendation reference article from the candidate reference historical articles corresponding to the historical articles according to the first attention degree values between the historical articles and corresponding candidate reference historical articles; and determining in a recommendable article set at least one candidate recommended article to be recommended to the target user based on the at least one recommendation reference article.

The memory 202 may include a program storage area and a data storage area. The program storage area may store an operating system, the program mentioned above, an application program required by at least one function (for example, a sound playback function and an image display function), and the like. The data storage area may store data created by the computer device and to-be-processed data, such as a user reading record, received by the computer device.

In addition, the memory 202 may include a high-speed random access memory, or may further include a non-volatile memory such as at least one magnetic disk storage device, a flash memory device, or another volatile solid-state storage device.

The communications interface 203 may be an interface of a communication module.

In this application, the computer device may further include the input unit 204 such as a keyboard.

The display 205 includes a display panel. In one possible case, the display panel may be configured in a form such as a liquid crystal display (LCD) or an organic light-emitting diode (OLED).

Certainly, a structure of the computer device shown in FIG. 2 does not constitute a limitation on the computer device in this embodiment of this application, and in an actual application, the computer device may include components that are more or fewer than those shown in FIG. 2, or a combination of some components.

Figure 3:
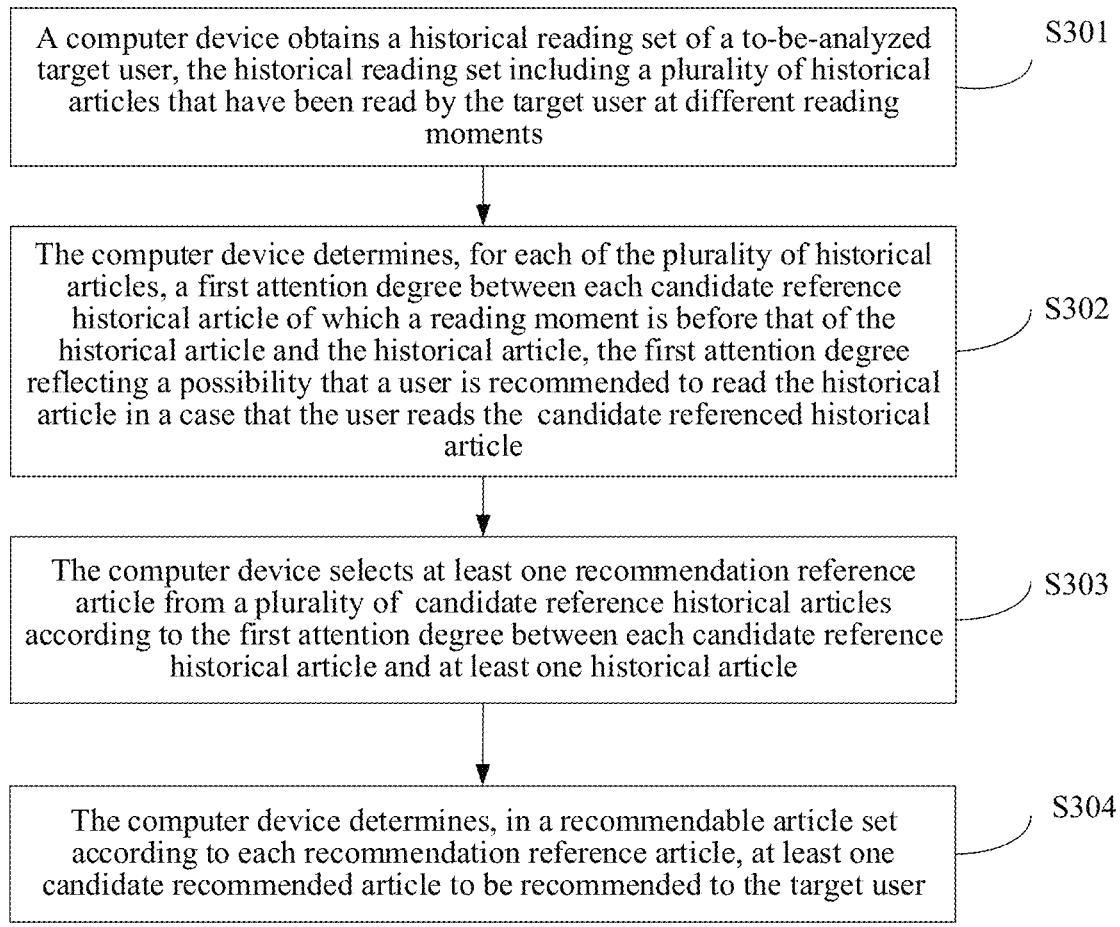
FIG. 3 shows a schematic flowchart of an article recommendation method according to an embodiment of this application.

With reference to the foregoing commonalities, an article recommendation method in the embodiments of this application is described. For example, FIG. 3 shows a schematic flowchart of an article recommendation method according to an embodiment of this application. This embodiment is described from a computer device side. This process includes:

S301. Obtain a historical reading article set of a to-be-analyzed target user.

The historical reading article set includes a plurality of historical articles that have been read by the target user at different reading moments.

For example, the historical reading article set includes a plurality of historical articles that are sorted in reading order. In this way, an order of reading moments corresponding to the plurality of historical articles may be determined according to the reading order of the plurality of historical articles.

For another example, the historical reading article set may include a plurality of historical articles that have been read by the target user and reading moments corresponding to the historical articles.

It may be understood that, for different users, articles suitable for recommendation to the users need to be determined with reference to historical reading article sets of the different users. In this embodiment of this application, for ease of description, a user for which to-be-recommended articles need to be determined currently is referred to as a to-be-analyzed target user. In addition, in distinction from an article recommended to the user, an article that has been read by a user is referred to as a historical article.

S302. A computer device determines, for each historical article, at least one candidate reference historical article of which a reading moment is before a reading moment of the historical article in the historical reading article set according to a content feature of the historical article.

It may be understood that, for any historical article in the historical reading article set, it may be considered that the target user reads the historical article as a result of reading other historical articles. A relationship between the other historical articles herein and the historical article may represent a focusing degree between the other historical articles and the historical article, that is, a possibility that a user is recommended, based on the other historical articles, to read the historical article. Therefore, in this application, other historical articles read by a user before the user reads a historical article need to be determined, and a relationship between corresponding historical articles is analyzed.

For example, a historical article set includes an article A, an article B, and an article C, and a sequence of the three articles represents a sequence in which the three articles are read by a user. As can be known, if the article A and the article B are read before the article C is read, it is likely that the article C is selected and read by the user after the user reads one or both of the article A and the article B. Therefore, the article A and the article B that are read before the article C may be determined, and a relationship between the article A and the article C and a relationship between the article B and the article C need to be analyzed, to obtain a possibility that the article A triggers the user to read the article C and a possibility that the article B triggers the user to read the article C.

For ease of distinction, the other historical articles that have been read before the historical article and that are used for analyzing relationships with the historical article are all referred to as candidate reference historical articles.

In this embodiment of this application, each candidate reference historical article that has been read before the historical article may be used as an candidate reference historical article, and a subsequent operation of analyzing a relationship between the candidate reference historical article and the historical articles is performed. Optionally, considering that a large quantity of articles have been read before the historical article, to reduce a volume of processed data without affecting a subsequent analysis result, a specified quantity of historical articles that have been read before the historical article may be used as candidate reference historical articles. For example, a specified quantity of historical articles are randomly selected from other historical articles that have been read before the historical article, so that the specified quantity of selected historical articles are used as the candidate reference historical articles, and a subsequent operation is performed.

Considering that other historical articles having reading moments that are close to a reading moment of the historical article have great impact on whether a user can read the historical article, a preset quantity of historical articles are randomly selected from a plurality of historical articles of which reading moments are before the reading moment of the historical article and of which durations between the reading moments and the reading moment of the historical article do not exceed a preset duration as the candidate reference historical articles, or a plurality of historical articles of which reading moments are closest to the reading moment of the historical article are selected as the candidate reference historical articles.

Considering that in the historical reading article set, there may be a case in which a quantity of articles that have been read before some historical articles is less than a preset quantity, for example, there is only one article before a historical article of which a reading moment ranks the second in the historical reading article set, in some implementations, a quantity of candidate reference historical articles corresponding to the historical article may be less than the preset quantity.

S303. The computer device determines, for each historical article, a first attention degree between the corresponding candidate reference historical article and the historical article according to a content feature of the historical article and a content feature of at least one candidate reference historical article corresponding to the historical article.

The attention degree may also be referred to as an attention degree value, a focusing degree, or a focusing degree value, and reflects a possibility that another article is recommend to the user when the user reads on article to read. In addition, the attention degree may alternatively reflect a possibility of choosing to read another article in a manner, such as clicking, when a user reads one article. Because of the foregoing meanings of the attention degree, the attention degree is also referred to as an attention degree or a focusing degree from one article to another article.

In this embodiment of this application, the attention degree may be a score, a probability, a level, or the like, and is not limited herein.

For ease of distinction from a subsequent attention degree between other articles, the attention degree between the candidate reference historical article and the historical article is referred to as a first attention degree. Correspondingly, the first attention degree is used for reflecting a possibility that a user is recommended to read the historical article when that the user reads the candidate reference historical article. In step S303, the computer device may determine the first attention degree between each candidate reference historical article and the historical article.

It may be understood that, for any article, a content feature of the article depends on a title of the article and words in a main body of the article, and the content feature of the article may reflect a category of the article, a theme of the article, specific content included in the article, and the like. Therefore, for any two articles, an attention degree from one article to the other article may be analyzed according to content features of the two articles.

In a possible implementation, for any two articles, based on respective content features of the two articles, the computer device may analyze a similarity between the content features of the two articles, and determine an attention degree between the two articles according to a similarity between the content features. For example, the similarity between the content features of the two articles is used as the attention degree between the two articles.

Correspondingly, the computer device determines a similarity between the candidate reference historical article and the historical article according to a content feature of the candidate reference historical article and a content feature of the historical article, and determines the attention degree between the candidate reference historical article and the historical article.

Particularly, in most cases, attention degrees between each article M in an article set and a specific article N need to be determined, and it is likely that a value relationship between the attention degrees between each article M in different article sets and the article N needs to be compared. In this case, for ease of comparing the attention degrees between each article M and the article N, for each article set, after a similarity between a content feature of each article in article set and a content feature of the article N is determined, normalization may be performed on the similarity between each article M in article set and the article N according to similarities corresponding to the article M in the article set, and a normalization result corresponding to the similarity between each article M in article set and the article N is used as an evaluation index for reflecting an attention degree.

After the computer device performs normalization on a similarity between a content feature of an article M and a content feature of an article N in the foregoing manner, a normalization result may be a value greater than or equal to 0 and less than 1, and a possibility that the reading of article M triggers a click on the article N may be reflected through the value.

In another possible implementation, the computer device may obtain, through training in advance, an attention model used for determining an attention degree. The attention model is obtained through training by using historical article sample sets of a plurality of users and marked attention score sequences respectively corresponding to historical article samples in each historical article sample set. For ease of distinguishing, a historical article for training the attention model is referred to as a historical article sample.

For a user, an attention score sequence corresponding to a historical article sample of the user includes: an attention score between each of a plurality of historical article samples that have been read by the user before the historical article sample is read and the historical article sample. For example, a historical reading log of a user is obtained from a server of an article publishing platform, to obtain other articles selected in a manner, such as clicking, when the user reads different articles, so that a possibility that reading of an article trigger the user to read other articles is computed, and the corresponding possibility is used as an attention score.

Correspondingly, in step S303, the computer device may determine an attention score between the candidate reference historical article and the historical article according to a content feature of the historical article and a content feature of at least one candidate reference historical article of having reading moments that are before a reading moment of the historical article in the historical reading article set by using an attention model obtained through training in advance.

In some implementations, a content feature of an article may be represented by an article vector of the article. Correspondingly, to determine an attention score from one or more articles M to the other article N, a content feature of each article (for example, the article M and the article N) may be first determined, and an article vector of the article is then determined. Then, article vectors of each article M and the article N are inputted into the attention model to output the attention score from each article M to the article N.

It may be understood that, for ease of subsequently comparing possibilities of recommending other historical articles according to different candidate reference historical articles, attention degrees (for example, attention scores) between candidate reference historical articles and a historical article outputted by the attention model may also be a result obtained through normalization.

Figure 4:
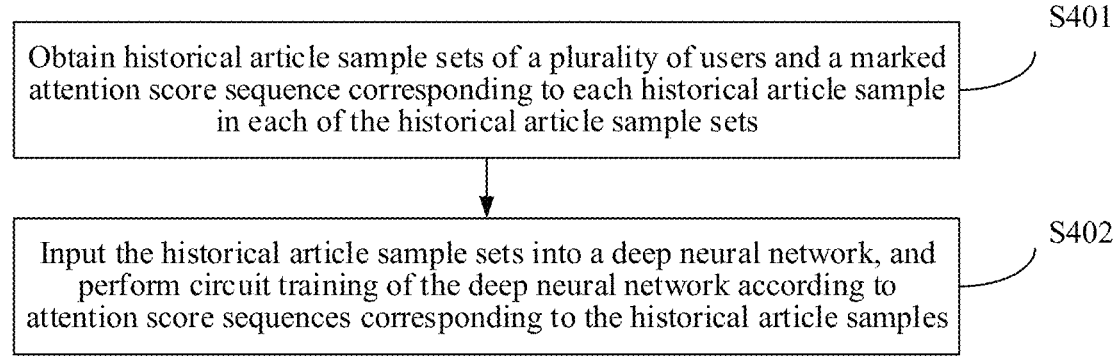
FIG. 4 shows a schematic flowchart of training an attention model in an article recommendation method according to an embodiment of this application.

There may be a plurality of processes of training the attention model according to the historical article sample set. This is not limited in this application. For ease of understanding, an example in which the attention model is obtained by training a deep neural network is used for illustration. For example, FIG. 4 shows a schematic flowchart of training an attention model.

In S401, the computer device obtains historical article sample sets of a plurality of users and a marked (or labeled) attention score sequence corresponding to each historical article sample in each of the historical article sample sets.

For example, a historical article sample set of a user includes an article S1, an article S2, an article S3, and an article S4 read by the user successively. A marked attention score sequence corresponding to the article S4 may include: an attention score between the article S4 and the article S3, an attention score between the article S4 and the article S2, and an attention score between the article S4 and the article S1. For the article S3, a corresponding marked attention score sequence may include: an attention score between the article S3 and the article S2, and an attention score between the article S3 and the article S1. For either of the articles S2 and S1, that is, a case in which there is only one or no article of which a reading moment is before a reading moment thereof, no attention score sequence may be set.

It may be understood that each attention score in a marked attention score sequence corresponding to a historical article sample is a result obtained by performing normalization according to each attention score in the attention score sequence.

In step S402, the computer device inputs each historical article sample into a deep neural network for training, and performs training of a deep neural network model according to attention score sequences of historical article samples until accuracy between an actual attention score sequence corresponding to each historical article sample outputted by the deep neural network and a corresponding marked attention score sequence satisfies a preset requirement.

For example, in a historical article sample set G, a marked attention score sequence corresponding to a historical article sample $S_m$ read by a user at a moment N is used as an example for illustration, and the marked attention score sequence corresponding to the historical article sample $S_m$ is attention scores between the historical article sample $S_m$ and a plurality of historical article samples in a historical article sample sequence S. The historical article sample sequence S is a sequence including a plurality of historical article samples read before the moment N in the historical article sample set G.

Correspondingly, the marked attention score sequence corresponding to the historical article sample $S_m$ may be represented as $A_m^* = \{a_1^*, a_2^*, \ldots, a_{m-1}^*\}$, where $a_j^*$ represents an attention score between the historical article sample $S_m$ and a historical article sample $S_j$ in the historical article sample sequence S, j represents a natural number from 1 to m−1, and m−1 represents a total quantity of historical article samples in the historical article sample sequence S.

The computer device inputs the historical article sample $S_m$ and the corresponding marked attention score sequence $A_m^*$ into the deep neural network model, the deep neural network model may output an actual attention score sequence $A_m$ corresponding to the historical article sample $S_m$, and the actual attention score sequence $A_m$ includes attention scores between the historical article sample $S_m$ outputted by the deep neural network model and historical article samples in the historical article sample sequence S.

In this way, upon comparison between the marked attention score sequence $A_m^*$ and the actual attention score sequence $A_m$ for a difference, whether accuracy of the deep neural network model meets a requirement may be analyzed. Optimization may be performed by using a gradient descent method according to a preset loss function and a marked attention score sequence corresponding to a plurality of historical article samples and an actual attention score sequence corresponding to the plurality of historical article samples until an iterative convergence. For example, the following loss function may be defined (that is, a formula 1):

$$L(A, A^*) = \sqrt{\sum_{m=1}^{n} (A_m - A_m^*)^2} \qquad \text{(formula 1)}$$

where values of m are different, $A_m^*$ and $A_m$ represent marked attention scores corresponding to different historical article samples and actual attention scores corresponding to the different historical article samples, and n is a total quantity of historical article samples for training.

Correspondingly, assuming that an optimization target is minL(A, A*), the computer device may optimize the optimization target by using a gradient descent method until final iterative convergence, at which time the training is ended. The deep neural network model obtained through training may be used as an attention model.

The attention model obtained through training also calculates a similarity between articles according to content features of different articles, and determines an attention degree between the articles.

For example, an example in which an attention degree between any article $d_i$ and an article $d_t$ in an article sequence (set) $D = \{d_1, d_2, \ldots d_i \ldots d_{t-2}, d_{t-1}\}$ is used for illustration. $d_i$ represents any article in an article sequence D, i is a natural number from 1 to t−1, and t−1 is a total quantity of articles in the article sequence D. To determine an attention degree between any article $d_i$ in the article sequence D and an article $d_t$, a function relationship of an attention score between the article $d_i$ in the article sequence D and the article $d_t$ may be represented as the following formula 2:

$$a_i = \frac{\exp(e_i)}{\sum_{j=1}^{t-1} \exp(e_j)} \qquad \text{(formula 2)}$$

$$\text{where} \quad e_i = F(Wh_{d_i} + Uh_{d_t} + b) \qquad \text{(formula 3)}$$

where $h_{d_i}$ is an article vector of the article $d_i$, and $h_{d_t}$ is an article vector of the article $d_t$. W, U, b are specified parameters in the attention model, and parameter values of the parameters are determined during a training process. F represents a specified function relationship, and the function relationship may also be determined during the training process.

For example, $$F(x) = \tanh x = \frac{\sinh x}{\cosh x} = \frac{e^x - e^{-x}}{e^x + e^{-x}};$$

and where $e_i$ represents a similarity between an article vector of the article $d_i$ and an article vector of the article $d_t$, and after normalization is performed through the formula 2, the attention score between the article $d_i$ and the article $d_t$ may be obtained.

For any article, there may alternatively be a plurality of manners of determining an article vector of the article based on a content feature of the article. For example, the computer device may perform word segmentation on content of the article, and input a plurality of words obtained through the word segmentation on the article into an article vector model obtained through training in advance, to output an article vector of the article through the article vector model.

For example, an example in which the article vector model including a long short-term memory (LSTM) network is used for illustration. To determine an article vector of an article d, first, word segmentation is performed on content of the article. Assuming that N words are obtained through the word segmentation on the article d, the article d may be represented as $d=\{w_1, w_2, \ldots, w_N\}$, where $w_i$, represents the i th component word, and i is a natural number from 1 to N. Then, the N component words are inputted into the LSTM network model in sequence, so that the article vector of the article d may be finally outputted through the LSTM network model.

Figure 5:
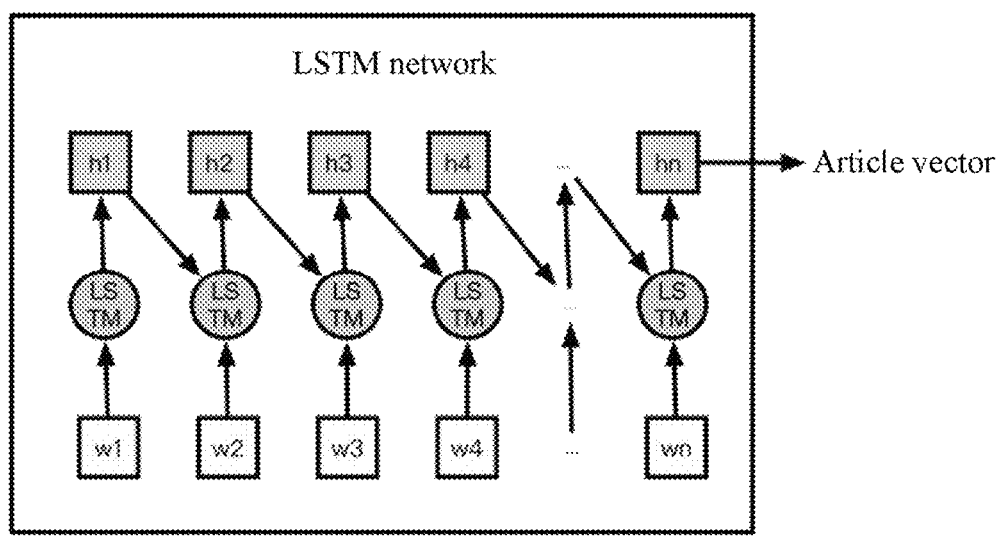
FIG. 5 shows a schematic diagram of outputting an article vector of an article based on a long-short term memory (LSTM) network according to an embodiment of this application.

For ease of understanding, FIG. 5 shows a schematic diagram of an LSTM network model for converting a plurality of component words of an article into an article vector of the article.

It can be learned from FIG. 5 that, component words obtained by performing word segmentation on an article are inputted in the LSTM network model, and an article vector of the article that is finally outputted is $h_t$.

S304. Select, according to the obtained attention degree between each of a plurality of the candidate reference historical articles and at least one historical article, at least one candidate reference historical article with a relatively low possibility of triggering to recommend an article to the target user as a recommendation reference article.

It may be understood that, in the historical reading article set of the target user, if the target user reads a historical article, a relatively low possibility of triggering to recommend other articles to the target user or triggering the target user to click to read other articles indicates a relatively low possibility of recommending an article to the target user based on the historical article before a current moment. In addition, because the historical article exists in the historical reading article set, the use is interested in content or other related information of the historical article, but seldom obtains an article with the related information. In this case, if articles are subsequently recommended to the target user based on the historical article, it necessarily helps expand articles read by the user and increase diversity of article recommendation.

For example, assuming that there are articles belong to categories, such as fashion, artsy, news and information, and science, in the historical reading article set of the target user, for two or more articles belonging to the same category or having similar content, an attention degree between the two or more articles belonging to the same category is determined, through the foregoing steps, to be relatively high. Therefore, if attention degrees between a specific candidate reference historical article and a plurality of historical articles are determined to be relatively high, it indicates that a possibility that the candidate reference historical article triggers to recommend an article is high, and there are a relatively large quantity of articles, in the historical reading article set, that belong to the category of the candidate reference historical article and that have content similar to that of the candidate reference historical article. Otherwise, if attention degrees between a specific candidate reference historical article and other articles are relatively low, it indicates that the target user has read a relatively small quantity of articles related to the category or the content of the candidate reference historical article. Therefore, the candidate reference historical article may be used as a recommendation reference article, to help increase diversity of articles recommended to the target user.

It may be understood that, each historical article corresponds to one or more candidate reference historical articles, and therefore, a plurality of candidate reference historical articles may be obtained in step S303. In addition, a historical article may be used as an candidate reference historical article of one or more other historical articles, and correspondingly, attention degrees between one candidate reference historical article and a plurality of historical articles may be determined. In this way, for each of the candidate reference historical articles, an attention degree between the candidate reference historical article and at least one historical article may be obtained. Therefore, for each of the candidate reference historical articles, a possibility of recommending an article to the target user based on the candidate reference historical article may be obtained with reference to the attention degrees between the candidate reference historical article and the corresponding historical articles.

For example, for an article 4, articles including an article 3, an article 2, and an article 1 may be used as candidate reference historical articles, and an attention degree between the article 3 and the article 4, an attention degree between the article 2 and the article 4, and an attention degree between the article 1 and the article 4 are separately determined, and for the article 3, articles including the article 2 and the article 1 may also be used as candidate reference historical articles, and an attention degree between the article 2 and the article 3 and an attention degree between the article 1 and the article 3 are separately determined. Correspondingly, for the article 3, only an attention degree between the article 3 and the article 4 is determined, and the attention degree may be used for reflecting a possibility of triggering, based on the article 3, to recommend an article to a user. For the article 2, a possibility of triggering, based on the article 2, to recommend an article to a user is comprehensively determined according to an attention degree between the article 2 and the article 4 and an attention degree between the article 2 and the article 3.

For any candidate reference historical article, there may be a plurality of manners of determining a possibility of recommending an article to a user based on the candidate reference historical article.

For example, in some implementations, for each of the candidate reference historical articles, according to an attention degree between the candidate reference historical article and at least one historical article (at least one historical article corresponding to the candidate reference historical article), an average attention degree between the candidate reference historical article and the at least one historical article is determined. Correspondingly, the average attention degree may reflect a possibility of recommending an article to a user based on the candidate reference historical article, and a lower average attention degree indicates a lower possibility of triggering to recommend an article to a user.

The computer device may select at least one candidate reference historical article with a relatively low average attention degree from a plurality of candidate reference historical articles corresponding to the plurality of historical articles as a recommendation reference article, to help subsequently determine, based on the recommendation reference article, an article that needs to be recommended to the target user. For example, an candidate reference historical article with a lowest average attention degree is selected as a recommendation reference article.

For example, after a first attention degree is determined for each of the plurality of the candidate reference historical articles, the first attention degrees of the candidate reference historical articles may be sorted to obtain a sorting result. If the first attention degrees are sorted in descending order, a category or content corresponding to an candidate reference historical article corresponding to a first attention degree that ranks higher in the sorting result is often read by a user, or a category or content of an candidate reference historical article corresponding to a first attention degree that ranks lower in the sorting result is seldom read by a user. In this case, the recommendation reference article may be determined according to requirements. If an candidate reference historical article corresponding to the last first attention degree in the sorting result is obtained, and the candidate reference historical article is used as the recommendation reference article, a category of articles that are seldom read may be recommended to the user according to the recommendation reference article. A quantity of recommendation reference articles specifically selected may be a specific percentage of a plurality of historical articles that have been read by the user, for example, 30%.

For ease of understanding, an example in which the computer device selects the recommendation reference article from the plurality of candidate reference historical articles based on the average attention degrees of the candidate reference historical articles is used for describing a process of determining the recommendation reference article in a historical article set in this application. For example, FIG. 6 shows a schematic diagram of an implementation of determining a recommendation reference article.

Figure 6:
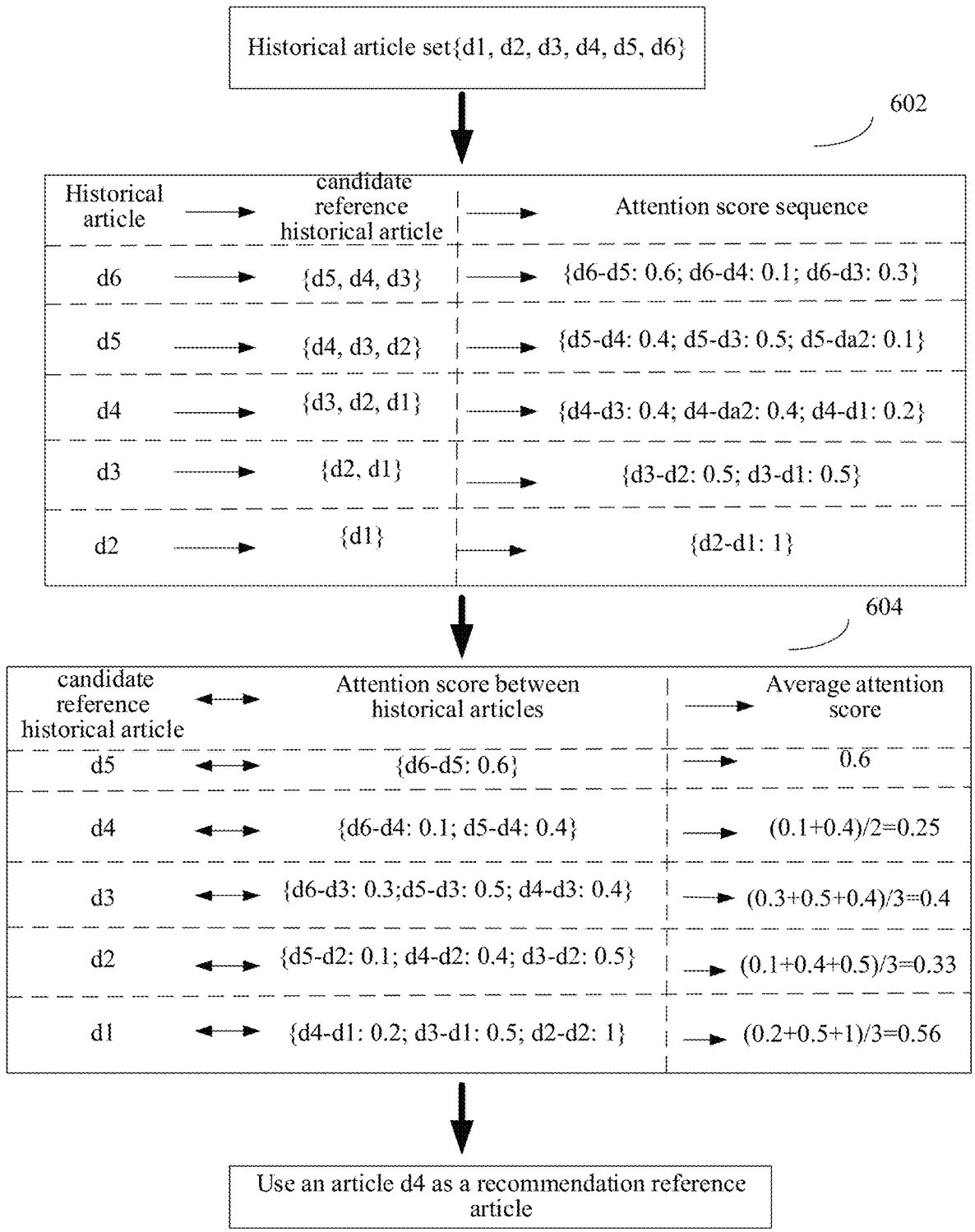
FIG. 6 illustrates and example implementation for determining a recommendation reference article.

In FIG. 6, an example in which the historical reading article set of the target user including an article d1, an article d2, an article d3, an article d4, an article d5, and an article d6 is used. In FIG. 6, an example in which for each article, no more than three articles that are read before the historical article is read are selected as candidate reference historical articles, and in addition, for ease of description, three articles of which reading moments are relatively close to the article are selected as candidate reference historical articles.

For example, in a part of "undetermined historical article" in FIG. 6, candidate reference historical articles corresponding to the article d6 include: the article d5, the article d4, and the article d3. Candidate reference historical articles corresponding to the article d5 include: the article d4, the article d3, and the article d2. Candidate reference historical articles corresponding to the article d4 include: the article d3, the article d2, and the article d1. Because there are less than three articles read before the article d3 and the article d2 are read, candidate reference historical articles corresponding to the article d3 only include the article d2 and the article d1, correspondingly, an candidate reference historical article corresponding to the article d2 is the article d1, and there is no other articles read before the article d1 is read, so that it is unnecessary to analyze an candidate reference historical article corresponding to the article d1.

Correspondingly, for each historical article, the computer device may calculate an attention score between the historical article and at least one candidate reference historical article corresponding to the historical article, to determine an attention score sequence corresponding to the historical article. Referring to the block 602 pointed by a first arrow from top to bottom in FIG. 6, an attention score between two articles is indicated by a number following a connecting line "-" connecting identifiers of the two articles. As shown in FIG. 6, for the article d6, an attention score between the article d6 and the article d5 is calculated, and the attention score is indicated by the number 0.6 following d6-d5 in FIG. 6. Correspondingly, an attention score d6-d4 between the article d6 and the article d4 is 0.1 m for example, and an attention score d6-d3 between the article d6 and the article d3 is 0.3. Similar for other articles d5, d4, d3, and d2, reference may be made to a part of "Attention score sequence" in FIG. 6 for details.

With reference to a correspondence between candidate reference historical articles and historical articles shown in the block 604 pointed by a second arrow from top to bottom in FIG. 6, it can be seen that each article may be used as the candidate reference historical article of a plurality of other articles. Block 604 shows a plurality of historical articles corresponding to each article that is used as an candidate reference historical article and attention scores between the candidate reference historical article and historical articles. For example, the article d5 is only an candidate reference historical article corresponding to the article d6, and an attention score d6-d5 between the article d5 and the article d6 can be found from an attention score sequence corresponding to the article d6, that is, the attention score d6-d5 between the article d5 and the article d6 is 0.6. Correspondingly, an average attention score corresponding to the article d5 is 0.6.

For another example, the article d4 is used as an candidate reference historical article of the article d6 and the article d5, where an attention score d6-d4 between the article d4 and the article d6 is 0.1, and an attention score d5-d4 between the article d4 and the article d5 is 0.4. It can be learned that an average attention score corresponding to the candidate reference historical article d4 is 0.25.

Similar to this, it may be seen as an example from FIG. 6 that an average attention score corresponding to the article d3 that is used as an candidate reference historical article is 0.4, an average attention score corresponding to the article d2 that is used as an candidate reference historical article is 0.33, and an average attention score corresponding to the article d1 that is used as an candidate reference historical article is 0.56.

It can be learned that for all candidate reference historical articles, the average attention score corresponding to the article d4 is the lowest, so that the article d4 is determined as a recommendation reference article, to help subsequently determine, based on the article d4, a candidate recommended article that needs to be recommended to the target user.

In another implementation, for the computer device, each candidate reference historical article may correspond to a preset quantity of historical articles by default. If a quantity of historical articles corresponding to an candidate reference historical article is less than the preset quantity, according to a difference between the preset quantity and the quantity of historical articles corresponding to the candidate reference historical article, a quantity of default attention degrees (for example, attention scores) are supplemented, the quantity being equal to the difference. Then, a sum of attention degrees between the candidate reference historical article and the preset quantity of historical articles is calculated, and the sum of the attention degrees is used as a basis for reflecting that the candidate reference historical article has a possibility of triggering to recommend an article.

For example, in FIG. 6 is, it attention scores between each candidate reference historical article and three historical articles may be determined, and a default attention score is 0.5. In FIG. 6, the article d5 is only an candidate reference historical article corresponding to the article d6. Therefore, a quantity of historical articles corresponding to the article 5 is less than a preset quantity, that is, 3. In this case, a sum of attention degrees corresponding to the article d5 may be a sum of the attention score between the article d5 and the article d6 and two default attention scores, specifically, 0.6+0.5+0.5=1.6. There are three historical articles corresponding to the article d3, that is, the article d6, the article d5, and the article d4. In this case, attention scores between the article d3 and the three historical articles may be directly added, an attention score corresponding to the article d3 after the addition is: 0.3+0.5+0.4=1.2. It can be learned that a possibility that the article d3 triggers to recommend an article is less than a possibility that the article d5 triggers to recommend an article.

S305. The computer device determines, in a recommendable article set according to a content feature of each recommendation reference article, at least one candidate recommended article to be recommended to the target user.

The recommendable article set includes a plurality of articles that can be recommended to the target user. For example, in an article publishing platform, the recommendable article set may be a set of all articles that can be published by the article publishing platform. For another example, the recommendable article set may alternatively be a set of articles that have been read by all users in the article publishing platform. Certainly, other possible cases may also exist, and are not limited herein.

For each recommendation reference article, there are a plurality of specific manners for the computer device to determine, based on the recommendation reference article, the candidate recommended article to be recommended to the target user. For example, in a possible implementation, the computer device may determine at least one candidate recommended article in the recommendable article set based on the content feature of the recommendation reference article in combination with a collaborative article recommendation algorithm, a content-based recommendation algorithm, or a sequence-based recommendation algorithm.

Optionally, to make a correlation between a category or content of the determined candidate recommended article and a category or content of the recommendation reference article higher, the computer device may further determine the candidate recommended article based on an attention-based recommendation policy. The attention-based recommendation policy is that: for each recommendation reference article, an attention degree between the recommendation reference article and each article in the recommendable article set may be determined according to a content feature of the recommendation reference article and a content feature of the article in the recommendable article set. Correspondingly, at least one candidate recommended article with a higher attention degree with the recommendation reference article may be selected from the recommendable article set.

When the candidate recommended article is determined, a plurality of candidate recommended articles may alternatively be determined. For example, after second attention degrees between all articles in the recommendable article set and at least one recommendation reference article are calculated, the obtained second attention degrees may be sorted, and a higher second attention degree indicates a higher possibility that a user reads the article after the user reads the recommendation reference article. For example, if two candidate recommended articles are determined in the recommendable article set, an article with a largest second attention degree and an article with a second largest second attention degree may be selected from the recommendable article set.

For a manner in which the computer device determines the attention degrees between the recommendation reference article and the articles in the recommendable article set, reference may be made to the preceding related descriptions of determining the attention degrees. For example, article vectors of the articles of the recommendable article set and an article vector of the recommendation reference article may be inputted into an attention model obtained through training in advance, to output an attention score sequence including the attention degrees (for example, the attention scores) between the recommendation reference article and the articles in the recommendable article set. Alternatively, the above-mentioned manner of determining the attention degree in another manner is also applicable herein, and details are not described herein.

It can be understood that in this embodiment of this application, for a historical article that has been read by a user, the computer device analyzes attention degrees between other historical articles that the user reads before the user reads the historical article and the historical article. An attention degree between two articles may reflect a possibility that a user is recommended to read the other article when the user reads one article. Therefore, a historical article representing a relatively low possibility of recommending an article to a target user may be determined in a historical reading article set according to the determined attention degrees between each article and other articles, and a category and content of the historical article do not belong to categories and content of articles that the user often reads. Therefore, a candidate recommended article is recommended to the user by using the historical article as a recommendation reference article, thereby improving diversity of the determined candidate recommended articles, and further improving diversity of articles recommended to the user.

It may be understood that after the candidate recommended article is determined based on the recommendation reference article, the computer device may directly use the candidate recommended article as an article that needs to be recommended to the target user. However, considering that a quantity of determined candidate recommended articles may be relatively large, and in an actual application, a plurality of recommendation policies may be configured, and a plurality of candidate recommended articles matching the recommendation reference article are determined according to different recommendation policies, resulting in a relatively large quantity of determined candidate recommended articles, if the large quantity of candidate recommended articles are recommended to a user, it is difficult to accurately recommend an article in which user is interested to the user, and consequently, a recommendation effect is affected.

Optionally, after determining at least one candidate recommended article according to the attention degrees between the articles in the recommendable article set and the recommendation reference article and based on one or more of manners such as a content recommendation algorithm and a collaborative recommendation algorithm, the computer device may further calculate, for each candidate recommended article, an attention degree between each historical article in a historical reading article set and the candidate recommended article to obtain an attention degree sequence between the candidate recommended article and a plurality of historical articles in the historical reading article set. Then, the computer device calculates an information entropy of the attention degree sequence corresponding to each of the candidate recommended articles, to obtain an information entropy corresponding to the candidate recommended article. Correspondingly, at least one candidate recommended article with a relatively small information entropy may be selected from the at least one candidate recommended article as at least one target recommended article to be recommended to the target user.

Optionally, after the information entropy of each candidate recommended article is determined, the information entropy may be sorted. A smaller information entropy indicates that a corresponding candidate recommended article is more preferentially pushed. If two target recommended articles need to be pushed, information entropies of candidate recommended articles are sorted, a candidate recommended article with a smallest information entropy and a candidate recommended article with a second smallest information entropy are obtained, and the two candidate recommended articles are used as the target recommended articles to be pushed to a user.

It may be understood that the attention degree between each historical article in the historical reading article set and the candidate recommended article may reflect a possibility that the historical article triggers to read the candidate recommended article, and the information entropy corresponding to the attention degree sequence between the candidate recommended article and each historical article in the historical reading article set may measure stability or reliability that each historical article in the historical reading article set triggers to read the candidate recommended article. It can be learned that selecting a corresponding candidate recommended article with a relatively small information entropy as a to-be-recommended target recommended article helps ensure, to the greatest extent, that articles that a user is interested in are recommended to the use while increasing diversity of articles recommended to the user, thereby implementing personalized recommendation based on the user.

After determining at least one target recommended article, the computer device may further determine a sequence of the at least one target recommended article, so that the article publishing platform subsequently outputs the at least one target recommended article according to the sequence.

Figure 7:
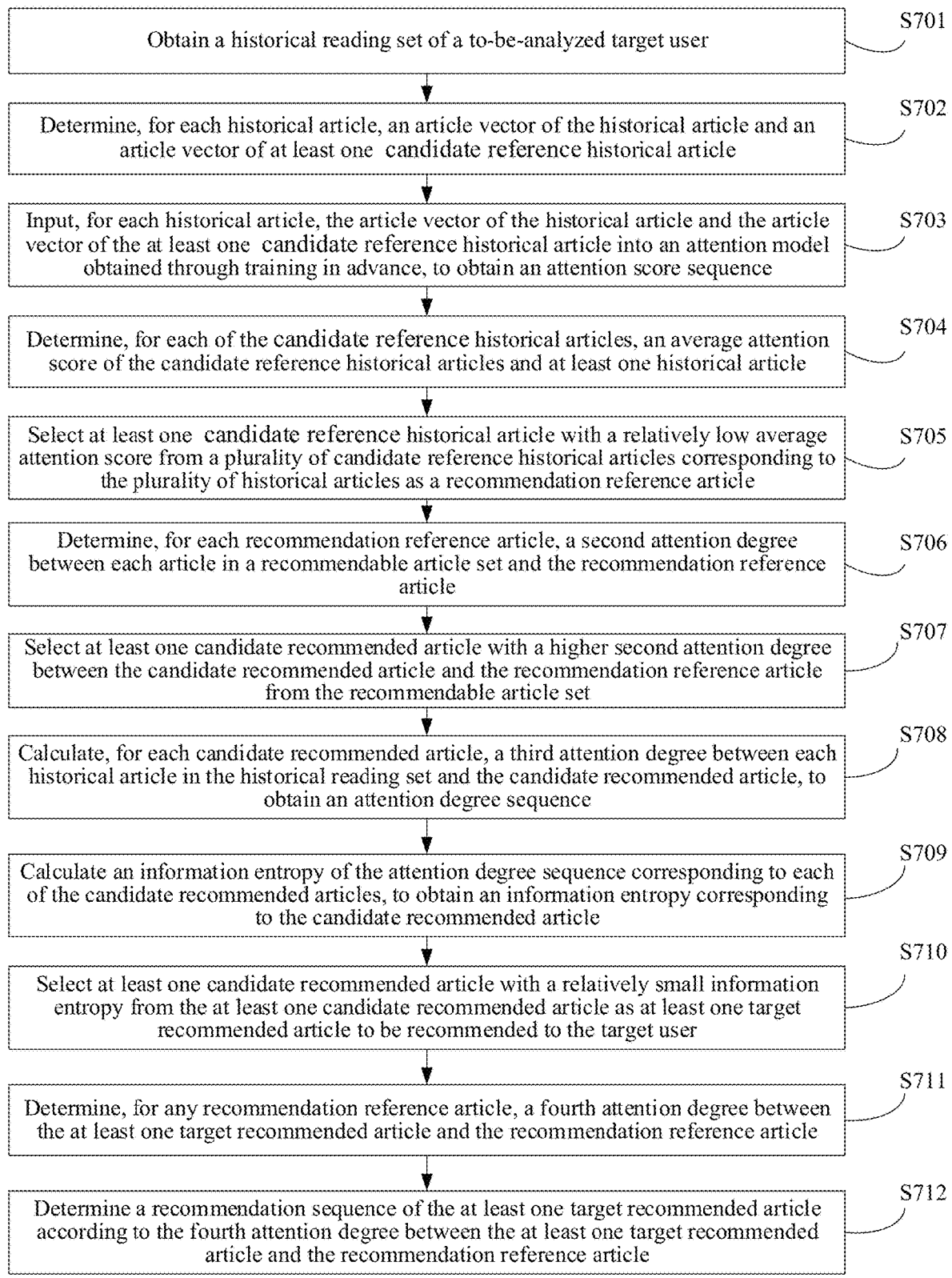
FIG. 7 shows another schematic flowchart of an article recommendation method according to an embodiment of this application.

For example, FIG. 7 shows another schematic flowchart of an article recommendation method according to an embodiment of this application. The method of this embodiment is described from a computer device side, and the method may include the following steps.

S701. A computer device obtains a historical reading article set of a to-be-analyzed target user.

The historical reading article set includes a plurality of historical articles that have been read by the target user at different reading moments.

S702. The computer device determines, for each historical article, an article vector of the historical article according to a content feature of the historical article, and determines an article vector of each candidate reference historical article according to a content feature of at least one candidate reference historical article having reading moments before a reading moment of the historical article in the historical reading article set.

S703. The computer device inputs, for each historical article, the article vector of the at least one candidate reference historical article corresponding to the historical article and a content vector of the historical article into an attention model obtained through training in advance, to output an attention score sequence through the attention model.

The attention score sequence includes an attention score between the at least one candidate reference historical article and the historical article. The attention score between the candidate reference historical article and the historical article may reflect a possibility that a user is recommended to read the historical article if the user reads the candidate reference historical article.

S704. The computer device determines, for each of the candidate reference historical articles, an average attention score from the candidate reference historical articles to at least one historical article according to the attention scores from the candidate reference historical articles to the at least one historical article.

S705. The computer device selects at least one candidate reference historical article with a relatively low average attention score from a plurality of the candidate reference historical articles corresponding to the plurality of historical articles as a recommendation reference article.

For steps S701 to S705, reference may be made to the foregoing related descriptions, and details are not described herein again. Steps S704 and S705 are only an implementation of determining a recommendation reference article based on an attention score between an candidate reference historical article and a corresponding historical article. Other manners mentioned in the foregoing embodiments are also applicable to this embodiment, and details are not described herein again.

It may be understood that the foregoing steps S701 to S705 are actually an attention model-based selection policy, that is, the recommendation reference article is selected from the historical reading article set of the target user based on the attention model. However, it may be understood that, in an actual application, selecting the recommendation reference article based on the attention model may not be the only selection policy of selecting a to-be-recommended article. Additionally or alternatively, the attention model-based selection policy configured in the computer device may include one or more other selection policies. For example, a user profile-based selection policy may also be configured. Specifically, one or more historical articles may be selected from the historical reading article set as the recommendation reference article based on a user profile of the target user. Correspondingly, the computer device may separately select recommendation reference articles through a plurality of configured selection policies, and perform subsequent operations.

Figure 8:
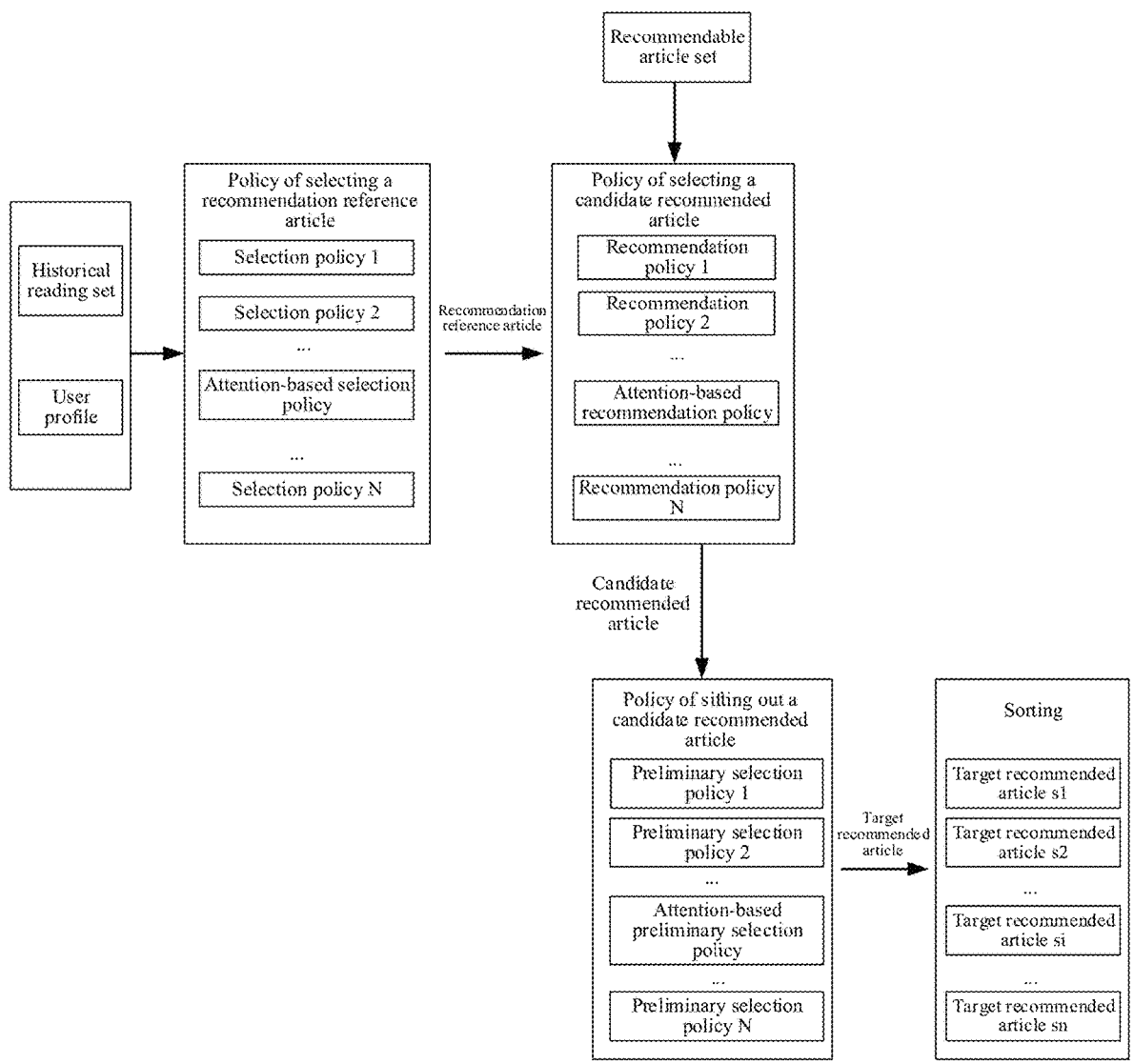
FIG. 8 illustrates and example implementation for of an article recommendation method according to an embodiment of this application.

For example, FIG. 8 shows a schematic diagram of an example implementation of an article recommendation method according to this application. It can be learned from FIG. 8 that there may be a plurality of recommendation policies for selecting a recommendation reference article. Correspondingly, the recommendation reference article is determined in the historical reading article set according to the historical reading article set read by the target user and a user profile of the target user of a user and by using a plurality of different recommendation policies separately. In this way, one recommendation reference article may be selected based on each recommendation policy.

Returning to S706 of FIG. 7, for each recommendation reference article, the computer device determines, a second attention degree between each article in the recommendable article set and the recommendation reference article according to a content feature of the recommendation reference article and a content feature of the article in the recommendable article set.

The second attention degree between any article in the recommendable article set and the recommendation reference article represents a possibility that a user is recommended to read the article in the recommendable article set if the user reads the recommendation reference article.

S707. The computer device selects at least one candidate recommended article with a higher second attention degree between the candidate recommended article and the recommendation reference article from the recommendable article set.

It may be understood that a higher attention degree between an article and a recommendation reference article indicates a higher association between a category and content of the article and a category and content of the recommendation reference article. The article belongs to a category of articles that the user has read but has seldom read. Selecting the article as a candidate recommended article not only can meet reading needs of the user, but also can increase diversity of articles read by the user.

In steps S706 and S707, actually, an example in which the candidate recommended article is determined through the attention-based recommendation policy is used for illustration. However, it may be understood that the manner of determining the candidate recommended article through other recommendation policies is also applicable to this embodiment.

It may be understood that in an actual application, when the computer device determines the candidate recommended article based on the recommendation reference article, it may set one recommendation policy, for example, the attention-based recommendation policy mentioned above. In an actual application, a plurality of recommendation policies may be set, for example, a content-based recommendation policy and a collaboration-based recommendation policy may be included while the attention-based recommendation policy is used. As shown in FIG. 8, a plurality of recommendation policies may also be configured. Correspondingly, the computer device may determine at least one candidate recommended article in a recommendable article set based on recommendation reference articles and the plurality of recommendation policies, or determine at least one candidate recommendation article with reference to the plurality of recommendation policies. As shown in FIG. 8, the candidate recommended article may be selected from the recommendable article set based on a plurality of recommendation policies and the determined recommendation reference article to help perform a subsequent preliminary selection operation.

S708. The computer device calculates, for each of the candidate recommended articles, a third attention degree between each historical article in the historical reading article set and the candidate recommended article, to obtain an attention degree sequence between a plurality of historical articles in the historical reading article set and the candidate recommended article.

The attention degree sequence includes third attention degrees between the candidate recommended article and a plurality of historical articles in the historical reading article set.

S709. The computer device calculates an information entropy of the attention degree sequence corresponding to each of the candidate recommended articles, to obtain an information entropy corresponding to the candidate recommended article.

The information entropy corresponding to the attention degree sequence may reflect a distribution of the attention degrees between the candidate recommended article and the historical articles in the historical reading article set. A smaller information entropy of the attention degree sequence corresponding to the candidate recommended article indicates a higher degree at which a user may be interested in the candidate recommended article and that is determined according to a historical reading article set read by the user.

There may be a plurality of other alternative manners of calculating the information entropy of the attention degree sequence. No limitation is imposed in this application.

For ease of understanding, an example information entropy calculating manner is described. For example, assuming that an attention degree sequence between a candidate recommended article and a historical article set is an attention score sequence, represented as $A_t = \{a_1, a_2 \ldots a_t\}$, an information entropy $H(A)$ corresponding to the attention score sequence may be calculated through the following formula:

$$H(A) = \sum_{i=1}^{t} a_i \log a_i \quad \text{(formula 4)}$$

where $a_t$ in the formula 4 is an attention score in the attention score sequence $A_t$.

S710. Select at least one candidate recommended article with a relatively small information entropy from the at least one candidate recommended article as at least one target recommended article to be recommended to the target user.

The computer device identifies a corresponding candidate recommended article with a relatively small information entropy as a target recommended article, so that the selected target recommended article can better match interests of a user while satisfying diversity.

It may be understood that steps S708 to S710 illustrate an example manner of determining, based on an attention model, a target recommended article selected from candidate recommended articles and recommended to the user. Step S708 to S710 thus illustrates an example attention model-based preliminary selection policy. However, it may be understood that, a manner of finally identifying at least one target recommended article from a plurality of candidate recommended articles through other preliminary selection policies is also applicable to this embodiment. For example, the preliminary selection policy may be based on selecting at least one target recommended article that best matches a user profile from a plurality of candidate recommended articles.

In an actual application, alternatively, at least one target recommended article may be finally identified from candidate recommended articles based on the attention model-based preliminary selection policy in combination with other preliminary selection policies. As shown in FIG. 8, a plurality of preliminary selection policies may be configured in the computer device. Correspondingly, the computer device may determine at least one target recommended article from candidate recommended articles based on the plurality of preliminary selection policies separately, or comprehensively determine at least one target recommended article with reference to the plurality of preliminary selection policies.

S711. The computer device determines, for any recommendation reference article, a fourth attention degree between the at least one target recommended article and the recommendation reference article.

The fourth attention degree reflects a possibility that a user is recommended to read the target recommended article if the user reads the recommendation reference article.

S712. The computer device determines a recommendation sequence of the at least one target recommended article according to the fourth attention degree between the at least one target recommended article and the recommendation reference article.

For example, a higher fourth attention degree corresponding to the target recommended article indicates that the target recommended article ranks higher. Particularly, when there are a plurality of recommendation reference articles, a comprehensive value of the fourth attention degrees of the target recommended article may be determined according to the fourth attention degrees between the target recommended article and the recommendation reference articles, and the recommendation sequence is determined according to the comprehensive value of the target recommended article.

A higher fourth attention degree corresponding to the target recommended article indicates a higher possibility that a user chooses to read the target recommended article if the user reads the recommendation reference article. Therefore, that a corresponding target recommended article with a higher fourth attention degree ranks higher is more favorable for a user to click the target recommended article.

It may be understood that after determining the recommendation sequence of the at least one target recommended article, the computer device may send an identifier of the at least one target recommended article and the recommendation sequence to an article publishing server. Correspondingly, when a target user accesses the article publishing server, for example, logs in to the article publishing server to read an article, the article publishing server may display the at least one target recommended article to the target user according to the recommendation sequence, so that the target user can see articles in wider categories that better match interests of the user.

It may be understood that the second attention degree, the third attention degree, and the fourth attention degree are merely used for ease of distinguishing attention degrees between different articles. However, for obtaining processes, reference may be made to the manner of determining the attention degree between articles described above, for example, the second attention degree, the third attention degree, and the fourth attention degree are determined by using the attention model obtained through training in advance. For details, refer to the related description in the foregoing embodiments. Details are not described herein again.

Figure 9:
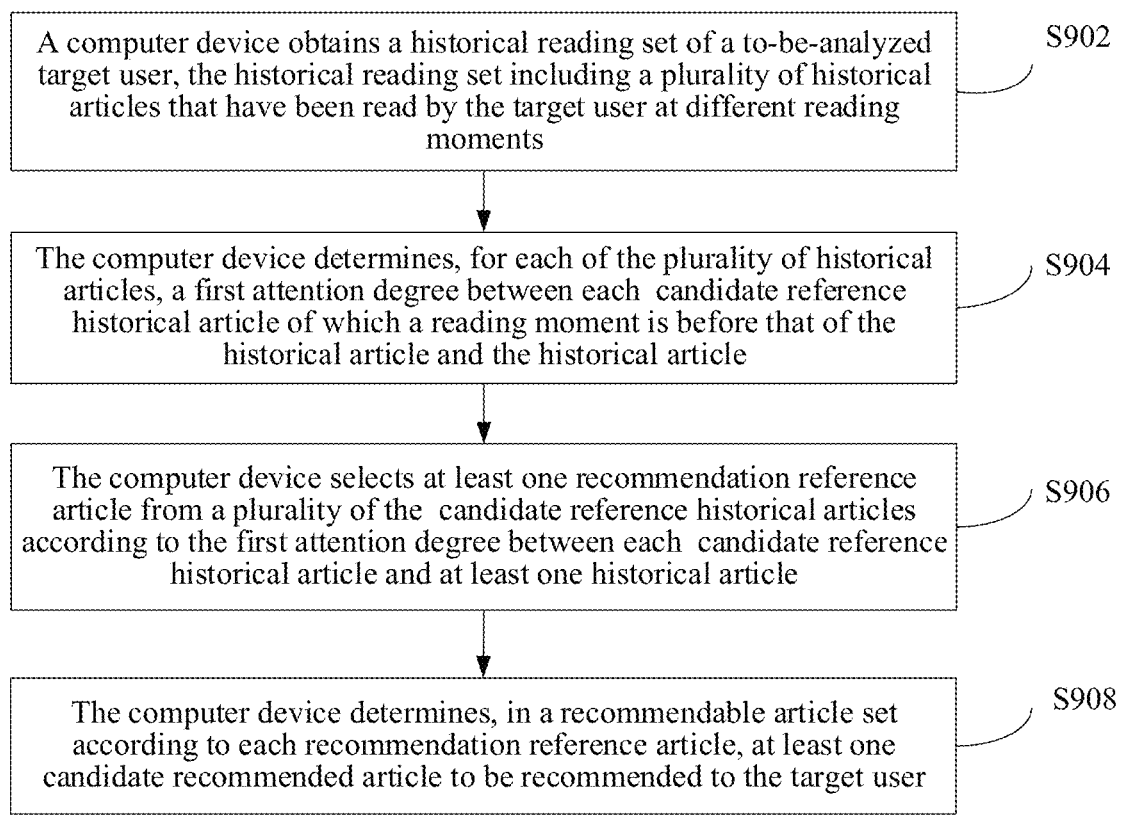
FIG. 9 shows a schematic flowchart of another article recommendation method according to an embodiment of this application.

In another aspect, this application further provides an article recommendation method. Optionally, as shown in FIG. 9, the article recommendation method includes the following steps.

S902. A computer device obtains a historical reading article set of a to-be-analyzed target user, the historical reading article set including a plurality of historical articles that have been read by the target user at different reading moments.

S904. The computer device determines, for each of the plurality of historical articles, a first attention degree between each candidate reference historical article of which a reading moment is before that of the historical article and the historical article, the first attention degree reflecting a possibility that a user is recommended to read the historical article if the user reads the candidate reference historical article.

S906. The computer device selects at least one recommendation reference article from a plurality of the candidate reference historical articles according to the first attention degree between each candidate reference historical article and at least one historical article.

S908. The computer device determines, in a recommendable article set according to each recommendation reference article, at least one candidate recommended article to be recommended to the target user.

Figure 10:
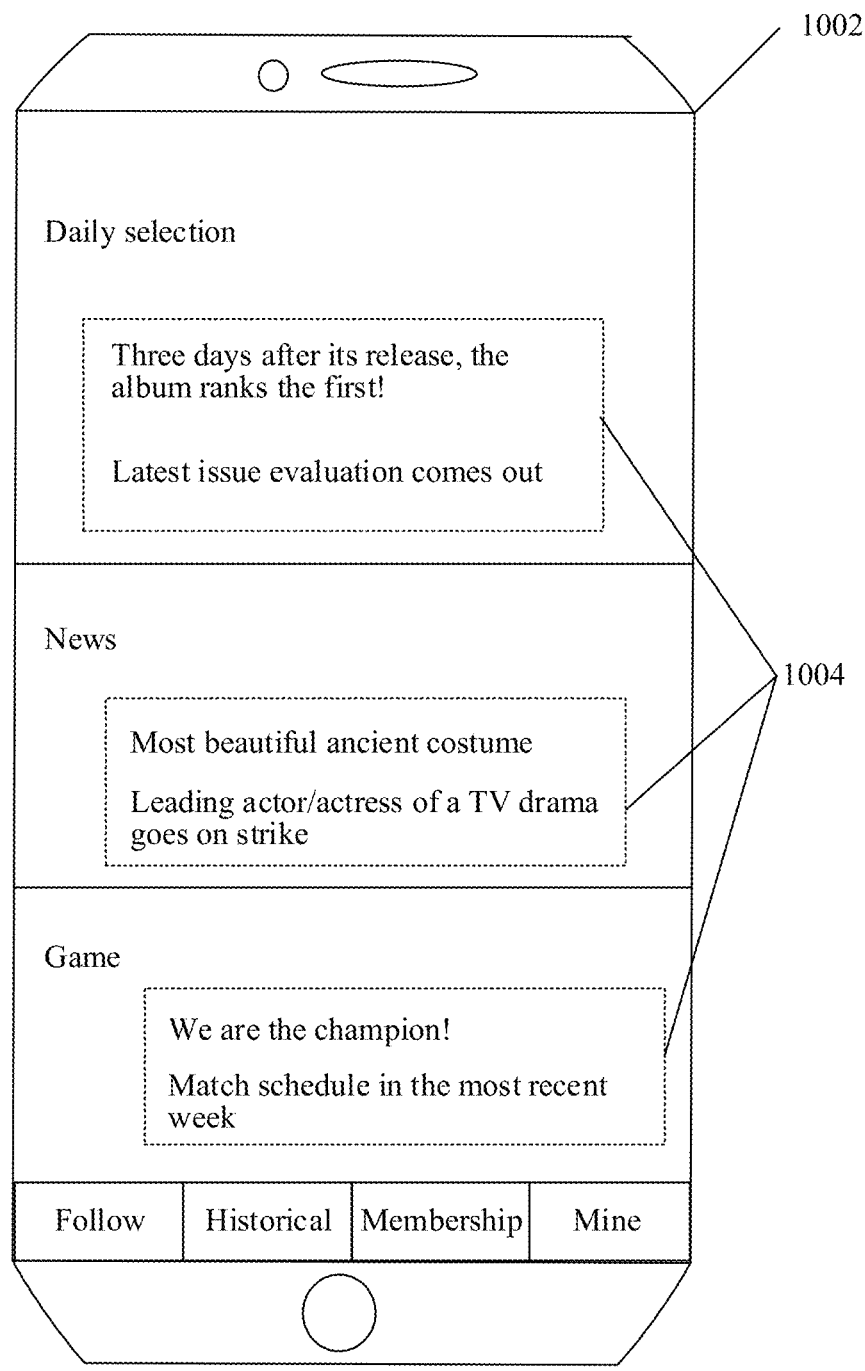
FIG. 10 shows an example display interface according to an embodiment of this application.

The following describes that the article recommendation method is applied to a specific recommendation process. The computer device is a mobile phone. As shown in FIG. 10, FIG. 10 is an optional browsing interface of a user. The user may log in to a client by using a terminal 1002 to browse articles. FIG. 10 shows an article 1004 that the client has recommended to the user according to an existing recommendation method. The user may read some articles by clicking a related article title or a link. During a reading process of the user, some reading records may be generated. The reading records include a read article and a reading moment. The reading records are included in a historical reading article set of the user. The historical reading article set includes a plurality of historical articles that have been read by the user.

After obtaining the plurality of historical articles, a mobile phone obtains an candidate reference historical article of each of the plurality of historical articles. The candidate reference historical article is an article of which a reading moment is before that of the historical article. For example, an example in which the plurality of historical articles include "We are the champion", "Match schedule", "Cast list", and "Ancient costume" is used. A reading sequence of the four historical articles is "We are the champion", "Match schedule", "Cast list", and "Ancient costume". Candidate reference historical articles of "Ancient costume" are three historical articles before "Ancient costume"; candidate reference historical articles of "Cast list" are two historical articles before "Cast list"; an candidate reference historical article of "Match schedule" is a historical article before "Match schedule"; and "We are the champion" has no candidate reference historical article. After determining the candidate reference historical article of each historical article, the mobile phone determines a first attention degree between each candidate reference historical article and a corresponding historical article. For example, Table (1) is provided, where a horizontal line "-" in Table 1 indicates that no first attention degree is included.

TABLE (1)

| First attention degree | We are the champion | Match schedule | Cast list | Ancient costume |
|---|---|---|---|---|
| We are the champion | — | 0.9 | 0.4 | 0.2 |
| Match schedule | — | — | 0.1 | 0.3 |
| Cast list | — | — | — | 0.8 |
| Ancient costume | — | — | — | — |

The various methods mentioned above may be used as a method for determining a first attention degree, and details are not described herein again. It can be learned that after a user reads "We are the champion", a possibility of reading "Match schedule" is relatively high, a possibility of reading "Cast list" is relatively low, and a possibility of reading "Ancient costume" is the lowest. For each of the candidate reference historical articles, for example, "We are the champion", a first attention degree between "We are the champion" and at least one historical article corresponding to "We are the champion" may be calculated. As calculated above, a first attention degree between "We are the champion" and "Match schedule" is 0.9, a first attention degree between "We are the champion" and "Cast list" is 0.4, and a first attention degree between "We are the champion" and "Ancient costume" is 0.2, so that an average value is 0.5. By using the same method, an average value of the first attention degree of each candidate reference historical article is obtained, that is, a first attention average value of "Match schedule" is 0.2, and a first attention average value of "Cast list" is 0.8.

Figure 11:
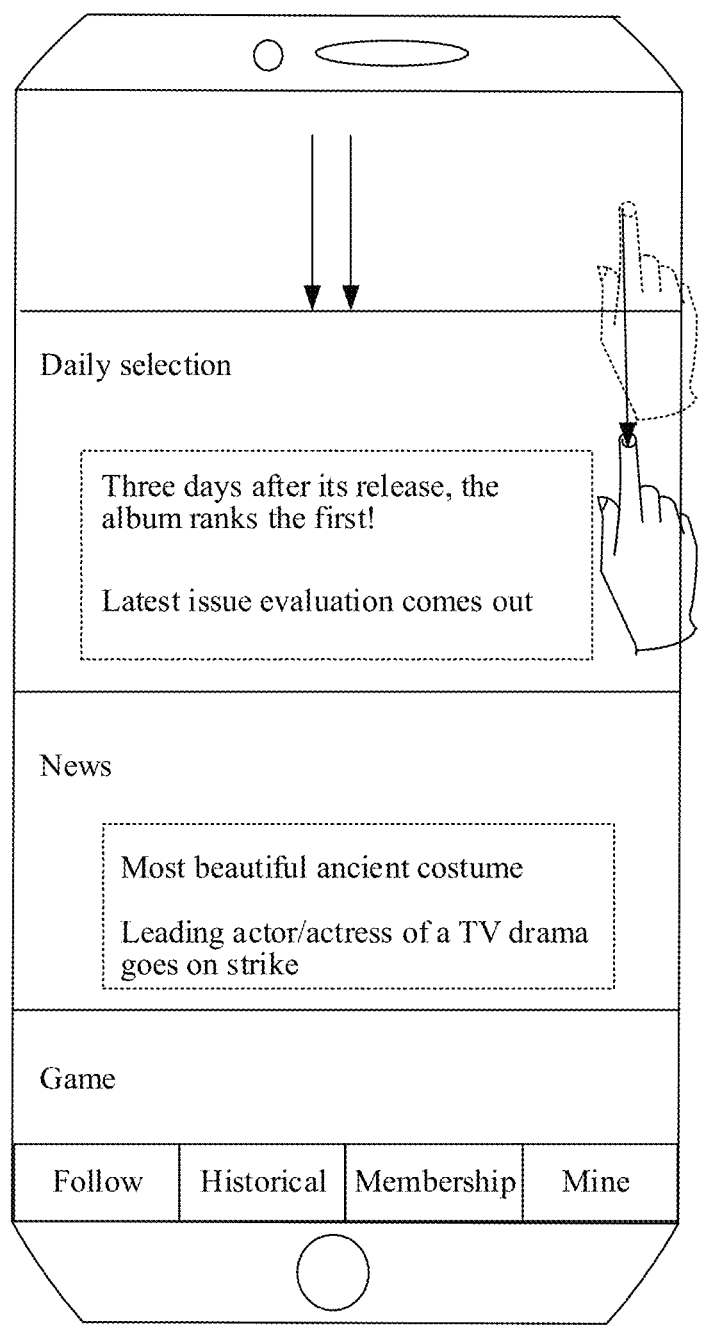
FIG. 11 shows another example display interface according to an embodiment of this application.
Figure 12:
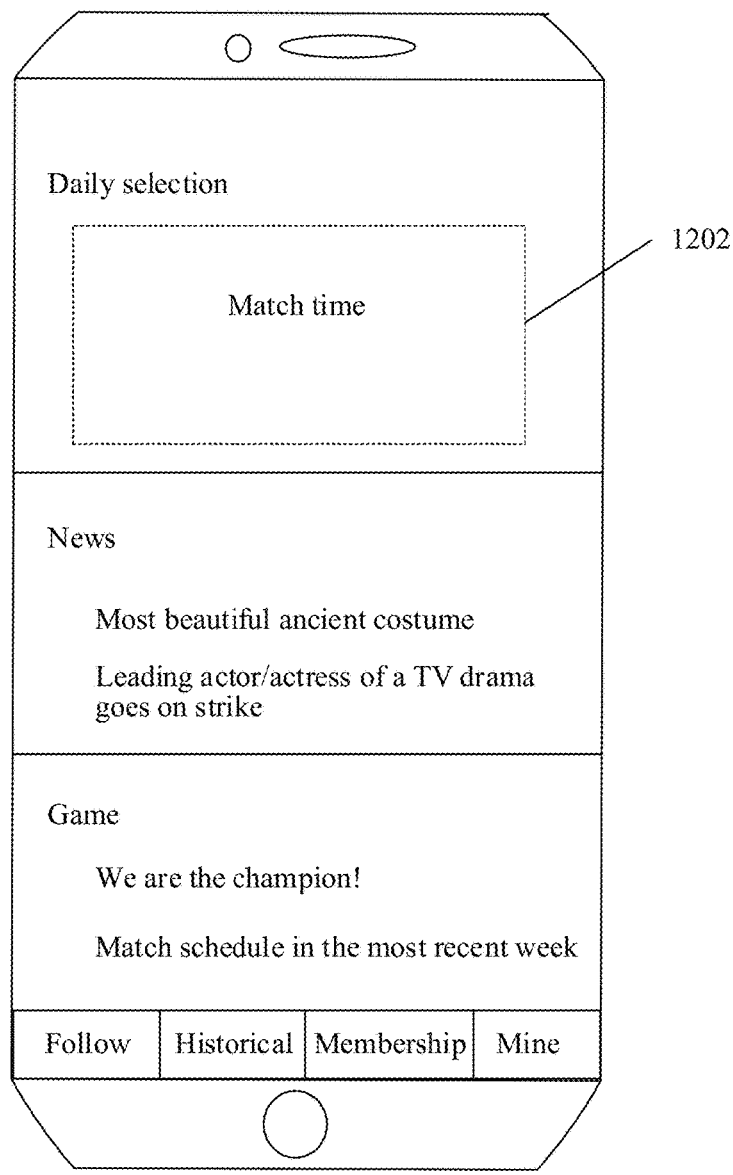
FIG. 12 shows yet another example display interface according to an embodiment of this application.

The mobile phone determines "Match schedule" with a lowest first attention average value in a plurality of the candidate reference historical articles as a recommendation reference article, and then, recommends a candidate recommended article in a recommendable article set according to the recommendation reference article "Match schedule". For example, if the recommendable article set includes "Match time" and "Director list", "Match time" may be used as a candidate recommended article. When a user obtains a recommended article, the candidate recommended article is recommended to the user. As shown in FIG. 11, a user requests a recommended article through a pull-down method. As shown in FIG. 12, a mobile phone recommends "Match time" to a user, and displays "Match time" in a recommendation area 1202.

In some other implementations, the average of the first attention value may be calculated with a predetermined number of first attention values ("three" for the example above). When the number of historical articles corresponding to an candidate reference historical articles is less than the predetermined number, then a predetermined value (e.g., 0.5) may be used for the missing historical articles. For example, the candidate reference historical article "cast list" above only corresponds to one historical article of "Ancient Costume" with a first attention value of 0.8. The average may then be calculated as averaging between 0.8, 0.5 and 0.5 wen the predetermined number is 3.

Figure 13:
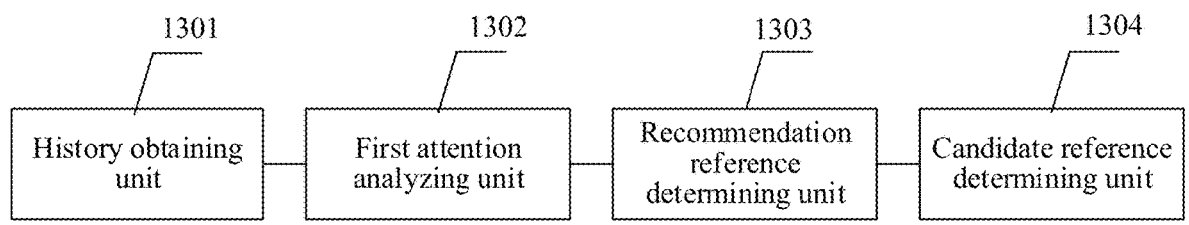
FIG. 13 shows a schematic diagram of an article recommendation apparatus according to an embodiment of this application.

According to another aspect, this application further provides an article recommended apparatus. For example, FIG. 13 shows a schematic diagram of components of an embodiment of an article recommendation apparatus according to this application. The apparatus in this embodiment may be applied to the foregoing computer device and may include:

a history obtaining unit 1301, configured to obtain a historical reading article set of a to-be-analyzed target user, the historical reading article set including a plurality of historical articles that have been read by the target user at different reading moments;

a first attention analyzing unit 1302, configured to determine, for each historical article, a first attention degree between the candidate reference historical article and the historical article according to a content feature of the historical article and a content feature of at least one candidate reference historical article of which a reading moment is before a reading moment of the historical article in the historical reading article set, the first attention degree reflecting a possibility that a user is recommended to read the historical article if the user reads the candidate reference historical article;

a recommendation reference determining unit 1303, configured to select, according to the obtained first attention degree between each of a plurality of the candidate reference historical articles and at least one historical article, at least one candidate reference historical article with a relatively low possibility of triggering to recommend an article to the target user as a recommendation reference article; and a candidate recommendation determining unit 1304, configured to determine, in a recommendable article set according to a content feature of each recommendation reference article, at least one candidate recommended article to be recommended to the target user.

Optionally, the first attention analyzing unit may include:

a first attention analyzing subunit, configured to determine an attention score between the candidate reference historical article and the historical article according to a content feature of the historical article and a content feature of at least one candidate reference historical article of which a reading moment is before a reading moment of the historical article in the historical reading article set by using an attention model obtained through training in advance.

The attention model is obtained through training by using historical article sample sets of a plurality of users and a marked attention score sequence corresponding to each historical article sample in each of the historical article sample sets, and the attention score sequence of the historical article sample includes an attention score between each of a plurality of historical article samples that a user reads before the user reads the historical article sample and the historical article sample.

Optionally, the first attention analyzing subunit may include:

a first vector determining subunit, configured to determine an article vector of the historical article according to the content feature of the historical article;

a second vector determining subunit, configured to determine an article vector of the candidate reference historical article according to the content feature of the at least one candidate reference historical article of which the reading moment is before the reading moment of the historical article in the historical reading article set; and an attention score analyzing subunit, configured to determine the attention score between the candidate reference historical article and the historical article according to the article vector of the historical article and the article vector of the at least one candidate reference historical article by using the attention model.

In a possible implementation, the recommendation reference determining unit includes:

an average attention analyzing subunit, configured to determine, for each of the candidate reference historical articles, an average attention degree from the candidate reference historical article to the at least one historical article according to the first attention degree between the candidate reference historical article and the at least one historical article; and a reference sifting subunit, configured to select at least one candidate reference historical article with a relatively low average attention degree from a plurality of the candidate reference historical articles corresponding to a plurality of historical articles as a recommendation reference article.

In a possible implementation, the candidate recommendation determining unit includes:

a second attention analyzing unit, configured to determine, for each recommendation reference article, a second attention degree between each article in the recommendable article set and the recommendation reference article according to a content feature of the recommendation reference article and a content feature of the article in the recommendable article set, the second attention degree reflecting a possibility that a user is recommended to read the article in the recommendable article set if the user reads the recommendation reference article; and a candidate recommendation selection unit, configured to select at least one candidate recommended article with a higher second attention degree between the candidate recommended article and the recommendation reference article from the recommendable article set.

Figure 14:
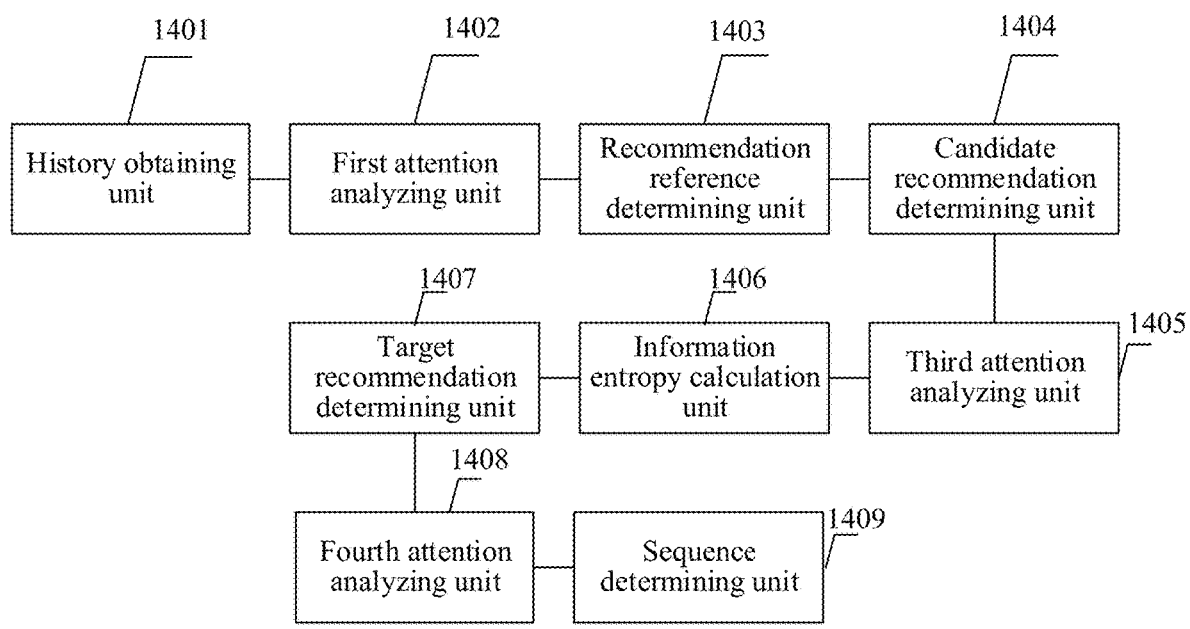
FIG. 14 shows a schematic diagram of another article recommendation apparatus according to an embodiment of this application.

For example, FIG. 14 shows a schematic diagram of another composition architecture of an article recommendation apparatus according to this application. The article recommendation apparatus in this embodiment differs from the apparatus shown in FIG. 13 as follows.

In addition to including a history obtaining unit 1401, a first attention analyzing unit 1402, a recommendation reference determining unit 1403, and a candidate recommendation determining unit 1404, the apparatus further includes:

a third attention analyzing unit 1405, configured to calculate, after at least one candidate recommended article is determined by the candidate recommendation determining unit and for each of the candidate recommended articles, a third attention degree between each historical article in the historical reading article set and the candidate recommended article, to obtain an attention degree sequence between a plurality of historical articles in the historical reading article set and the candidate recommended article, the third attention degree reflecting a possibility that a user is recommended to read the candidate recommended article if the user reads the historical article in the historical reading article set;

an information entropy calculation unit 1406, configured to calculate an information entropy of the attention degree sequence corresponding to each of the candidate recommended articles, to obtain an information entropy corresponding to the candidate recommended article; and a target recommendation determining unit 1407, configured to select at least one candidate recommended article with a relatively small information entropy from the at least one candidate recommended article as at least one target recommended article to be recommended to the target user.

Optionally, the apparatus may further include:

a fourth attention analyzing unit 1408, configured to determine a fourth attention degree between the recommendation reference article and at least one target recommended article, the fourth attention degree reflecting a possibility that a user is recommended to read the target recommended article if the user reads the recommendation reference article; and a sequence determining unit 1409, configured to determine a recommendation sequence of the at least one target recommended article according to the fourth attention degree between the recommendation reference article and the at least one target recommended article.

For details of the history obtaining unit 1401, the first attention analyzing unit 1402, the recommendation reference determining unit 1403, and the candidate recommendation determining unit 1404, reference may be made to related descriptions of the foregoing embodiments, and the details are not described herein again.

According to still another aspect of the embodiments of this application, a storage medium is further provided. The storage medium stores a computer program, the computer program being configured to perform steps in any one of the method embodiments when being run.

Optionally, in this embodiment, the storage medium may be configured to store a computer program used for performing the following steps:

S1. Obtain a historical reading article set of a to-be-analyzed target user, the historical reading article set including a plurality of historical articles that have been read by the target user at different reading moments.

S2. Determine, for each historical article, a first attention degree between the candidate reference historical article and the historical article according to a content feature of the historical article and a content feature of at least one candidate reference historical article of which a reading moment is before a reading moment of the historical article in the historical reading article set, the first attention degree reflecting a possibility that a user is recommended to read the historical article if the user reads the candidate reference historical article.

S3. Select, according to the obtained first attention degree between each of a plurality of the candidate reference historical articles and at least one historical article, at least one candidate reference historical article with a relatively low possibility of triggering to recommend an article to a user as a recommendation reference article.

S4. Determine, in a recommendable article set according to a content feature of each recommendation reference article, at least one candidate recommended article to be recommended to the target user.

Alternatively, in this embodiment, the storage medium may be configured to store a computer program used for performing the following steps:

S1. A computer device obtains a historical reading article set of a to-be-analyzed target user, the historical reading article set including a plurality of historical articles that have been read by the target user at different reading moments.

S2. The computer device determines, for each of the plurality of historical articles, a first attention degree between each candidate reference historical article of which a reading moment is before that of the historical article and the historical article, the first attention degree reflecting a possibility that a user is recommended to read the historical article if the user reads the candidate reference historical article.

S3. The computer device selects at least one recommendation reference article from a plurality of the candidate reference historical articles according to the first attention degree between each candidate reference historical article and at least one historical article.

S4. The computer device determines, in a recommendable article set according to each recommendation reference article, at least one candidate recommended article to be recommended to the target user.

Optionally, in this embodiment, a person of ordinary skill in the art may understand that all or some of the steps of the methods in the foregoing embodiments may be implemented by a program instructing relevant hardware of a terminal device. The program may be stored in a computer-readable storage medium. The storage medium may include a flash disk, a read-only memory (ROM), a random access memory (RAM), a magnetic disk, an optical disc, and the like.

The embodiments in this specification are all described in a progressive manner. Each embodiment focuses on a difference from other embodiments. For same or similar parts in the embodiments, refer to the embodiments. An apparatus embodiment is basically similar to a method embodiment, and therefore is described briefly. For related parts, refer to partial descriptions in the method embodiment.

Finally, in this specification, relational terms, such as first and second, are only used for distinguishing one entity or operation from another, and do not necessarily require or imply that any actual relationship or sequence exists between the entities or operations. Moreover, the terms "include", "comprise", or their any other variant are intended to cover a non-exclusive inclusion, so that a process, a method, an article, or a device that includes a list of elements not only includes those elements but also includes other elements that are not expressly listed, or further includes elements inherent to such a process, method, article, or device. An element preceded by "includes a . . . " does not, without more constraints, preclude the existence of additional identical elements in the process, method, article, or device that includes the element.

The above description of the disclosed embodiments enables a person skilled in the art to implement or use this application. Various modifications to the embodiments are obvious to the person skilled in the art, and general principles defined in this specification may be implemented in other embodiments without departing from the spirit or scope of this application. Therefore, this application will not be limited to the embodiments described in this specification, but extends to the widest scope that complies with the principles and features with novelty disclosed in this specification.

The foregoing descriptions are merely optional implementations of this application. A person of ordinary skill in the art may make several improvements and refinements without departing from the principle of this application and the improvements and refinements shall fall within the protection scope of this application.

In the embodiments of this application, for a historical article that has been read by a user, the computer device analyzes attention degrees between other historical articles that the user reads before the user reads the historical article and the historical article. An attention degree between two articles may reflect a possibility that a user is recommended to read the other article if the user reads one article. Therefore, a historical article representing a relatively low possibility of recommending an article to a target user may be determined in a historical reading article set according to the determined attention degrees between each article and other articles, and a category and content of the historical article do not belong to categories and content of articles that the user often reads. Therefore, a candidate recommended article is recommended to the user by using the historical article as a recommendation reference article, thereby improving diversity of the determined candidate recommended articles, and further improving diversity of articles recommended to the user.

What is claimed is:

1. An article recommendation method, comprising:
   obtaining, by a computer device, a historical reading article set of a to-be-analyzed target user, the historical reading article set comprising a plurality of historical articles that have been read by the target user at different reading moments;
   determining, by the computer device, for each historical article of the plurality of historical articles, first attention degree values between the each historical article and candidate reference historical articles having reading moments before that of the each historical article, the first attention degree values reflecting a probability that a user is recommended to read the historical article if the user has read the candidate reference historical articles;
   selecting, by the computer device, at least one recommendation reference article from the candidate reference historical articles corresponding to the historical articles according to the first attention degree values between the historical articles and corresponding candidate reference historical articles; and
   determining, by the computer device, in a recommendable article set at least one candidate recommended article to be recommended to the target user based on the at least one recommendation reference article.

2. The article recommendation method according to claim 1, wherein determining, by the computer device for each historical article, the first attention degree values between the each historical article and the candidate reference historical article comprises:
   determining, by the computer device, attention scores between the each historical article and the candidate reference historical articles according to a content feature of the each historical article and content features of the candidate reference historical articles using a pre-trained attention model,
   wherein the pre-trained attention model is trained using historical article sample sets of a plurality of users labeled with attention score sequences corresponding to each historical article sample in each of the historical article sample sets, each of the attention score sequences corresponding to the historical article samples comprising a sequence of attention scores between a historical article sample and other historical article samples that a user reads before the user reads the historical article sample.

3. The article recommendation method according to claim 2, wherein determining, by the computer device, the attention scores between the each historical article and the candidate reference historical articles using the pre-trained attention model comprises:

determining, by the computer device, an article vector of the each historical article according to the content feature of the historical article;

determining, by the computer device, article vectors of the candidate reference historical articles according to the content features of the candidate reference historical articles; and determining, by the computer device, the attention scores between the each historical article and the candidate reference historical articles according to the article vector of the each historical article and the article vectors of the candidate reference historical articles by using the pre-trained attention model.

4. The article recommendation method according claim 1, wherein selecting, by the computer device, the at least one recommendation reference article from the candidate reference historical articles according to the first attention degree values comprises:

determining, by the computer device, for each of the candidate reference historical articles, an average attention degree value using the first attention degree values associated with the each of the candidate reference historical articles; and sorting, by the computer device, average attention degree values of the candidate reference historical articles in ascending order, obtaining a predetermined number (X) of candidate reference historical articles corresponding to first X average attention degree values after the sorting, and determining the X candidate reference historical articles as the at least one recommendation reference articles.

5. The article recommendation method according to claim 1, wherein determining, by the computer device in the recommendable article set the at least one candidate recommended article comprises:

determining, by the computer device, for each recommendation reference article, second attention degree values between articles in the recommendable article set and the each recommendation reference article according to a content feature of the each recommendation reference article and content features of the articles in the recommendable article set, the second attention degree values reflecting a probability that a user is recommended to read the articles in the recommendable article set if the user has read the each recommendation reference article; and sorting, by the computer device, the second attention degree values of the articles in the recommendable article set in descending order, to obtain a sorting result, obtaining a predetermined number (Y) of articles from the recommendable article set corresponding to first Y second attention degree values in the sorting result, and determining the Y articles as the candidate recommended articles.

6. The article recommendation method according to claim 1, wherein after the determining, by the computer device, the at least one candidate recommended article, the method further comprises:

calculating, by the computer device, for each of the at least one candidate recommended articles, third attention degree values between the plurality of historical articles in the historical reading article set and the each candidate recommended article, to obtain an attention degree value sequence, the third attention degree values reflecting a probability that a user is recommended to read the each candidate recommended article if the user has read the plurality of historical articles in the historical reading article set;

calculating, by the computer device, an information entropy of the attention degree value sequence corresponding to the each candidate recommended article; and sorting, by the computer device, the information entropies of the candidate recommended articles in ascending order, obtaining a predetermined number (Z) of candidate recommended articles corresponding to first Z information entropies after the sorting, and determining the Z candidate recommended articles as target recommended articles to be recommended to the target user, Z being determined according to a quantity of the candidate recommended articles.

7. The article recommendation method according to claim 6, wherein after the sorting, by the computer device, the information entropies of the candidate recommended articles in ascending order, obtaining Z candidate recommended articles corresponding to first Z information, and determining the Z candidate recommended articles as target recommended articles to be recommended to the target user, the method further comprises:

determining, by the computer device, fourth attention degree values between the at least one recommendation reference article and the target recommended articles, the fourth attention degree values reflecting a probability that a user is recommended to read the target recommended articles if the user has read the at least one recommendation reference articles; and determining a recommendation sequence of the target recommended articles according to the fourth attention degree values.

8. An article recommendation apparatus comprising a memory for storing computer instructions and a processor configured to execute the computer instructions to:

obtain a historical reading article set of a to-be-analyzed target user, the historical reading article set comprising a plurality of historical articles that have been read by the target user at different reading moments;

determine, for each historical article of the plurality of historical articles, first attention degree values between the each historical article and candidate reference historical article having reading moments before that of the each historical article, the first attention degree values reflecting a probability that a user is recommended to read the historical article if the user has read the candidate reference historical article;

select at least one recommendation reference article from the candidate reference historical articles corresponding to the historical articles according to the first attention degree values between the historical articles and corresponding candidate reference historical article; and determine, in a recommendable article set, at least one candidate recommended article to be recommended to the target user based on the at least one recommendation reference article.

9. The article recommendation apparatus according to claim 8, wherein the processor, when executing the computer instructions to determine, for each historical article, the first attention degree values between the each historical article and the candidate reference historical article, is configured to:
determine attention scores between the each historical article and the candidate reference historical article according to a content feature of the each historical article and content features of the candidate reference historical article using a pre-trained attention model,
wherein the pre-trained attention model is trained by using historical article sample sets of a plurality of users labeled with attention score sequences corresponding to each historical article sample in each of the historical article sample sets, each of the attention score sequences corresponding to the historical article samples comprising a sequence of attention scores between a historical article sample and other historical article samples that a user reads before the user reads the historical article sample.

10. The article recommendation apparatus according to claim 8, wherein the processor, when executing the computer instructions to select the at least one recommendation reference article from the candidate reference historical articles according to the first attention degree values, is configured to:
determine, for each of the candidate reference historical articles, an average attention degree value using the first attention degree values associated with the each of the candidate reference historical article; and
sort average attention degree values of the candidate reference historical articles in ascending order, obtain a predetermined number (X) of candidate reference historical articles corresponding to first X average attention degree values after the sorting, and determine the X candidate reference historical articles as the at least one recommendation reference articles.

11. The article recommendation apparatus according to claim 8, wherein processor, when executing the computer instructions to determine in the recommendable article set the at least one candidate recommended article, is configured to:
determine, for each recommendation reference article, second attention degree values between articles in the recommendable article set and the each recommendation reference article according to a content feature of the each recommendation reference article and content features of the articles in the recommendable article set, the second attention degree values reflecting a probability that a user is recommended to read the articles in the recommendable article set if the user has read the recommendation reference article; and
sort the second attention degree values of the articles in the recommendable article set in descending order, to obtain a sorting result, obtain a predetermined number (Y) of articles from the recommendable article set corresponding to first Y second attention degree values in the sorting result, and determine the Y articles as the candidate recommended articles.

12. The article recommendation apparatus according to claim 11, the processor is further configured to, after determining the at least one candidate recommended article:
calculate, for each of the at least one candidate recommended articles, third attention degree values between the plurality of historical articles in the historical reading article set and the each candidate recommended article, to obtain an attention degree value sequence, the third attention degree values reflecting a probability that a user is recommended to read the each candidate recommended article if the user has read the plurality of historical articles in the historical reading article set;
calculate an information entropy of the attention degree value sequence corresponding to the each candidate recommended article; and
sort the information entropies of the candidate recommended articles in ascending order, obtain a predetermined number (Z) candidate recommended articles corresponding to first Z information entropies after the sorting, and determine the Z candidate recommended articles as target recommended articles to be recommended to the target user, Z being determined according to a quantity of the candidate recommended articles.

13. The article recommendation apparatus according to claim 12, wherein the processor is further configured to execute the computer instructions to:
determine a fourth attention degree values between the at least one recommendation reference article and the target recommended articles, the fourth attention degree values reflecting a probability that a user is recommended to read the target recommended article if the user has read the at least one recommendation reference articles; and
determine a recommendation sequence of the target recommended articles according to the fourth attention degree values.

14. A computer-readable non-transitory storage medium, storing a computer program, the computer program, when executed by a processor, is configured to cause the processor to:
obtain a historical reading article set of a to-be-analyzed target user, the historical reading article set comprising a plurality of historical articles that have been read by the target user at different reading moments;
determine, for each historical article of the plurality of historical articles, first attention degree values between the each historical article and candidate reference historical article having reading moments before that of the each historical article, the first attention degree values reflecting a probability that a user is recommended to read the historical article if the user has read the candidate reference historical article;
select at least one recommendation reference article from the candidate reference historical articles corresponding to the historical articles according to the first attention degree values between the historical articles and corresponding candidate reference historical article; and
determine, in a recommendable article set, at least one candidate recommended article to be recommended to the target user based on the at least one recommendation reference article.

15. The computer-readable non-transitory storage medium of claim 14, wherein the computer program, when executed by the processor to determine, for each historical article, the first attention degree values between the each historical article and the candidate reference historical article, is configured to cause the processor to:

determine attention scores between the each historical article and the candidate reference historical article according to a content feature of the each historical article and content features of the candidate reference historical article using a pre-trained attention model, wherein the pre-trained attention model is trained by using historical article sample sets of a plurality of users labeled with attention score sequences corresponding to each historical article sample in each of the historical article sample sets, each of the attention score sequences corresponding to the historical article samples comprising a sequence of attention scores between a historical article sample and other historical article samples that a user reads before the user reads the historical article sample.

16. The computer-readable non-transitory storage medium of claim 14, wherein the computer program, when executed by the processor to select the at least one recommendation reference article from the candidate reference historical articles according to the first attention degree values, is configured to cause the processor to:
   determine, for each of the candidate reference historical articles, an average attention degree value using the first attention degree values associated with the each of the candidate reference historical article; and
   sort average attention degree values of the candidate reference historical articles in ascending order, obtain a predetermined number (X) of candidate reference historical articles corresponding to first X average attention degree values after the sorting, and determine the X candidate reference historical articles as the at least one recommendation reference articles.

17. The computer-readable non-transitory storage medium of claim 14, wherein the computer program, when executed by the processor to determine in the recommendable article set the at least one candidate recommended article, is configured to cause the processor to:
   determine, for each recommendation reference article, second attention degree values between articles in the recommendable article set and the each recommendation reference article according to a content feature of the each recommendation reference article and content features of the articles in the recommendable article set, the second attention degree values reflecting a probability that a user is recommended to read the articles in the recommendable article set if the user has read the recommendation reference article; and
   sort the second attention degree values of the articles in the recommendable article set in descending order, to obtain a sorting result, obtain a predetermined number (Y) of articles from the recommendable article set corresponding to first Y second attention degree values in the sorting result, and determine the Y articles as the candidate recommended articles.

18. The computer-readable non-transitory storage medium of claim 17, wherein the computer program, is configured to cause the processor to, after determining the at least one candidate recommended article:
   calculate, for each of the at least one candidate recommended articles, third attention degree values between the plurality of historical articles in the historical reading article set and the each candidate recommended article, to obtain an attention degree value sequence, the third attention degree values reflecting a probability that a user is recommended to read the each candidate recommended article if the user has read the plurality of historical articles in the historical reading article set;
   calculate an information entropy of the attention degree value sequence corresponding to the each candidate recommended article; and
   sort the information entropies of the candidate recommended articles in ascending order, obtain a predetermined number (Z) candidate recommended articles corresponding to first Z information entropies after the sorting, and determine the Z candidate recommended articles as target recommended articles to be recommended to the target user, Z being determined according to a quantity of the candidate recommended articles.

\* \* \* \* \*